(12) United States Patent
Matsuura et al.

(10) Patent No.: US 12,080,408 B2
(45) Date of Patent: Sep. 3, 2024

(54) INFORMATION PROCESSING SYSTEM, AND INFORMATION PROCESSING METHOD AND PROGRAM

(71) Applicant: Sony Group Corporation, Tokyo (JP)

(72) Inventors: Hiromitsu Matsuura, Tokyo (JP); Takeshi Maeda, Tokyo (JP); Takuya Nakamura, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 227 days.

(21) Appl. No.: 17/775,585

(22) PCT Filed: Nov. 24, 2020

(86) PCT No.: PCT/JP2020/043694
§ 371 (c)(1),
(2) Date: May 10, 2022

(87) PCT Pub. No.: WO2021/106883
PCT Pub. Date: Jun. 3, 2021

(65) Prior Publication Data
US 2022/0384022 A1  Dec. 1, 2022

(30) Foreign Application Priority Data
Nov. 28, 2019  (JP) .................... 2019-215768

(51) Int. Cl.
*G06F 3/14*    (2006.01)
*G16H 40/20*   (2018.01)
*H04N 7/18*    (2006.01)

(52) U.S. Cl.
CPC .............. *G16H 40/20* (2018.01); *G06F 3/14* (2013.01); *H04N 7/183* (2013.01)

(58) Field of Classification Search
CPC ....... G06F 16/74; G06F 3/14; G06T 2200/24; H04N 21/47; H04N 21/472; H04N 21/488; H04N 21/4882
See application file for complete search history.

(56) References Cited

U.S. PATENT DOCUMENTS 11,769,207 B2 *  9/2023  Wolf .................... G16H 50/20
2015/0302150 A1 * 10/2015  Mazar .................. G16H 40/63
                                                        705/2

(Continued)

FOREIGN PATENT DOCUMENTS

JP    2013-117881 A    6/2013
JP    2014-209350 A    11/2014
(Continued)

OTHER PUBLICATIONS

International Search Report and Written Opinion mailed on Feb. 9, 2021, received for PCT Application PCT/JP2020/043694, Filed on Nov. 24, 2020, 8 pages including English Translation.

(Continued)

*Primary Examiner* — Antonio A Caschera
(74) *Attorney, Agent, or Firm* — XSENSUS LLP

(57) ABSTRACT

Efficiency of a surgery-related service can be further improved. An information processing system according to an embodiment includes a surgery information acquisition unit that acquires information regarding a surgery, and a display control unit that displays a surgery process area indicating an entire process of the surgery and a progress of the entire process, and a work process area indicating a work content of a part of the entire process and a progress of the work content. The display control unit calculates at least one of the progress of the entire process and the progress of the work content according to information regarding a surgery different from the surgery.

16 Claims, 22 Drawing Sheets

(56) References Cited

U.S. PATENT DOCUMENTS

2020/0315708 A1* 10/2020 Mosnier .................. G16H 50/20
2021/0093329 A1*  4/2021 Poltaretskyi ........... A61B 34/10

FOREIGN PATENT DOCUMENTS

JP    2015-197757 A    11/2015
WO   2005/084570 A1    9/2005

OTHER PUBLICATIONS

Marutani et al., "Development of Surgical Skills Training System to Teach Expert Physicians Skill Appropriate for Surgical Process", The Institute of Electronics Information and Communication Engineers, IEICE Technical Report, vol. 116, No. 38, May 19-20, 2016, pp. 53-58 (9 pages including English Abstract).

* cited by examiner

FIG.3
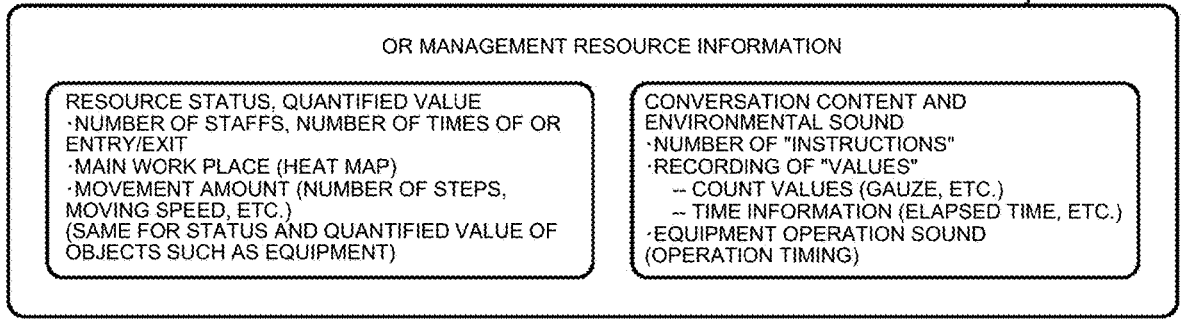
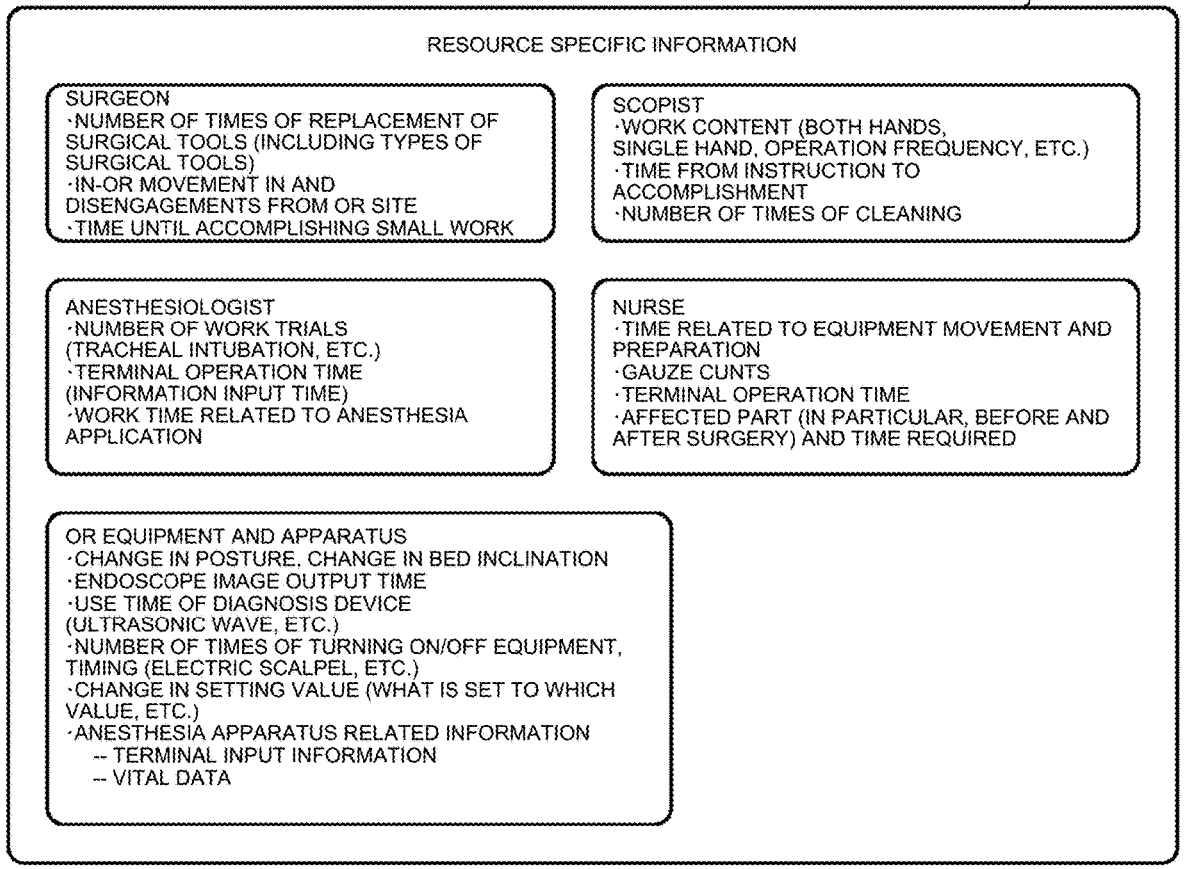

FIG.10

PROGRESS STATUS DISPLAY AREA

| ENTIRE PROCESS (105%) | | | | | | | | | |
|---|---|---|---|---|---|---|---|---|---|
| PREPARATION (102%) | | | | SURGERY (110%) | | | | POST TREATMENT (98%) | |
| EQUIPMENT PREPARATION (97%) | ANESTHESIA INDUCTION (100%) | PREPARATION BEFORE SURGERY (102%) | TIMEOUT (102%) | ENDOSCOPE INSERTION (99%) | GALLBLADDER CUTTING: CHOLECYSTECTOMY (120%) | CLEANING | INSTRUMENT REMOVAL (99%) | WOUND CLOSURE | POST SURGICAL TREATMENT (98%) | ANESTHETIC AWAKENING (97%) | CLEANING AND ARRANGEMENT (99%) |

| PREPARATION OF RESOURCES NECESSARY FOR ANESTHESIA INDUCTION | | |
|---|---|---|
| PATIENT | : INFORMATION TRANSFER STATUS | : OK (10 MINUTES PREVIOUS TRANSFER) |
| ANESTHE-SIOLOGIST | : IN-ROOM STATUS | : NG (ENTERING ROOM AFTER 20 MINUTES) |
| ANESTHESIA APPARATUS | : OPERATING STATE | : OK (OPERATING FROM 10 MINUTES AGO) |

PREPARATION OF RESOURCES NECESSARY FOR ANESTHESIA INDUCTION

| PATIENT | : INFORMATION TRANSFER STATUS | : OK (10 MINUTES PREVIOUS TRANSFER) |
|---|---|---|
| ANESTHE-SIOLOGIST | : IN-ROOM STATUS | : OK (ENTERED 10 MINUTES AGO) |
| ANESTHESIA APPARATUS | : OPERATING STATE | : OK (OPERATING FROM 10 MINUTES AGO) |

PREPARATION OF RESOURCES NECESSARY FOR PREPARATION BEFORE SURGERY

| XXX0 | :YYY | :OK |
|---|---|---|
| XXX1 | :YYY | :OK |

•
•
•

PREPARATION OF RESOURCES NECESSARY FOR STARTING SURGERY

| SURGEON | : IN-ROOM STATUS | : NG (ENTERING AFTER 40 MINUTES) |
|---|---|---|
| SCOPIST | : IN-ROOM STATUS | : OK (ENTERED 10 MINUTES AGO) |

| MEDICAL DEPARTMENT | DATE | CASE NO. | SURGERY COST |
|---|---|---|---|
| NEUROSURGERY | YYYY/MM/DD | 00001 | NNNNN(±NNN) |
| NEUROSURGERY | YYYY/MM/DD | 00002 | NNNNN(±NNN) |
| NEUROSURGERY | YYYY/MM/DD | 00003 | NNNNN(±NNN) |
| NEUROSURGERY | YYYY/MM/DD | 00004 | NNNNN(±NNN) |
| ⋮ | ⋮ | ⋮ | ⋮ |

FIG.24

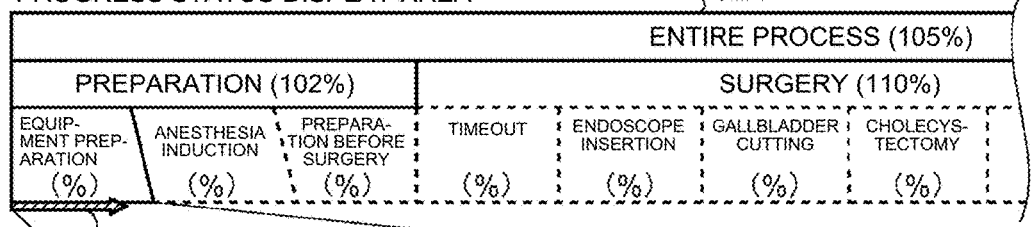

| MONITOR | CARRY-IN STATUS | :OK, | CONNECTION STATUS | :OK |
| CCU | CARRY-IN STATUS | :OK, | CONNECTION STATUS | :OK |
| ELECTRIC SCALPEL | CARRY-IN STATUS | :OK, | CONNECTION STATUS | :OK |
| HEART-LUNG MACHINE | CARRY-IN STATUS | :OK, | CONNECTION STATUS | :OK |
| SUCTION CLEANING DEVICE | CARRY-IN STATUS | :OK, | CONNECTION STATUS | :OK |
| ECHO | CARRY-IN STATUS | :OK, | CONNECTION STATUS | :OK |
| ENDOSCOPE | CARRY-IN STATUS | :NG, | CONNECTION STATUS | :NG |
| MACHINE STAND | CARRY-IN STATUS | :OK, | CONNECTION STATUS | :OK |

INFORMATION PROCESSING SYSTEM, AND INFORMATION PROCESSING METHOD AND PROGRAM

CROSS-REFERENCE TO RELATED APPLICATIONS

The present application is based on PCT filing PCT/JP2020/043694, filed Nov. 24, 2020, which claims priority to Japanese Patent Application No. 2019-215768, filed Nov. 28, 2019, the entire contents of each are incorporated herein by reference.

FIELD

The present disclosure relates to an information processing system and an information processing method and program.

BACKGROUND

In recent years, with diversification and complication of surgery, costs related to surgery have dramatically increased in hospitals. On the other hand, there is a fact that a hospital obtains more than half of the benefit by surgery. Under such circumstances, hospitals have paid attention not only to the number of surgeries but also to cost reduction by improving the quality and efficiency of the surgery.

For example, the following Patent Literatures 1 and 2 provide a conventional technique intended to improve the efficiency of surgery.

Patent Literature 1 discloses a technique of displaying a calculated revenue and expenditure and the movement mode. A camera is provided in a surgery-related facility, and a surgery execution time is calculated from the movement mode of a doctor, medical staff, equipment, and so on detected by the camera. The revenue and expenditure in surgery is calculated from the calculated surgery execution time and a time unit price such as manpower cost.

CITATION LIST

Patent Literature

Patent Literature 1: JP 2014-209350 A
Patent Literature 2: JP 2015-197757 A

SUMMARY

Technical Problem

However, in Patent Literature 1, it is possible to determine delay of individual work, but it is difficult to identify which work is delayed in the entire process. Thus, it is difficult to sufficiently improve efficiency of the surgery-related service.

In addition, by linking information on surgery-related facility acquired by the camera and in-hospital database, it is possible to display the movement mode of doctors and the like and the manpower cost in a combined manner. However, since status of doctors, medical staff, equipment, and so on are displayed only with numerical figures such as a duration and a flow line, it is difficult to extract a problem in view of the actual situation. Thus, it is difficult to sufficiently improve efficiency of the surgery-related service.

Therefore, an object of the present disclosure is to provide an information processing system and an information processing method and program capable of further improving the efficiency of surgery-related service.

Solution to Problem

To solve the above-described problem, an information processing system according to one aspect of the present disclosure comprises: a surgery information acquisition unit that acquires information regarding a surgery; and a display control unit that executes control for displaying a surgery process area that indicates an entire process of the surgery and a degree of progress of the entire process, and a work process area that indicates a work content of a part of the entire process and a degree of progress of the work content, wherein the display control unit calculates at least one of the degree of progress of the entire process and the degree of progress of the work content based on information regarding a surgery different from the surgery.

BRIEF DESCRIPTION OF DRAWINGS

FIG. 3 is a schematic diagram illustrating an example of resource information accumulated in a database according to the embodiment of the present disclosure.

FIG. 10 is a diagram illustrating a specific example of a progress status display area according to the embodiment of the present disclosure.

FIG. 15 is a diagram for explaining Usage Example 1 according to the embodiment of the present disclosure (part 2).

FIG. 17 is a diagram for explaining Usage Example 2 according to the embodiment of the present disclosure (part 2).

FIG. 23 is a diagram illustrating Usage Example 6 according to the embodiment of the present disclosure (Part 3).

FIG. 24 is a diagram illustrating Usage Example 7 according to the embodiment of the present disclosure.

DESCRIPTION OF EMBODIMENTS

Figure 1:
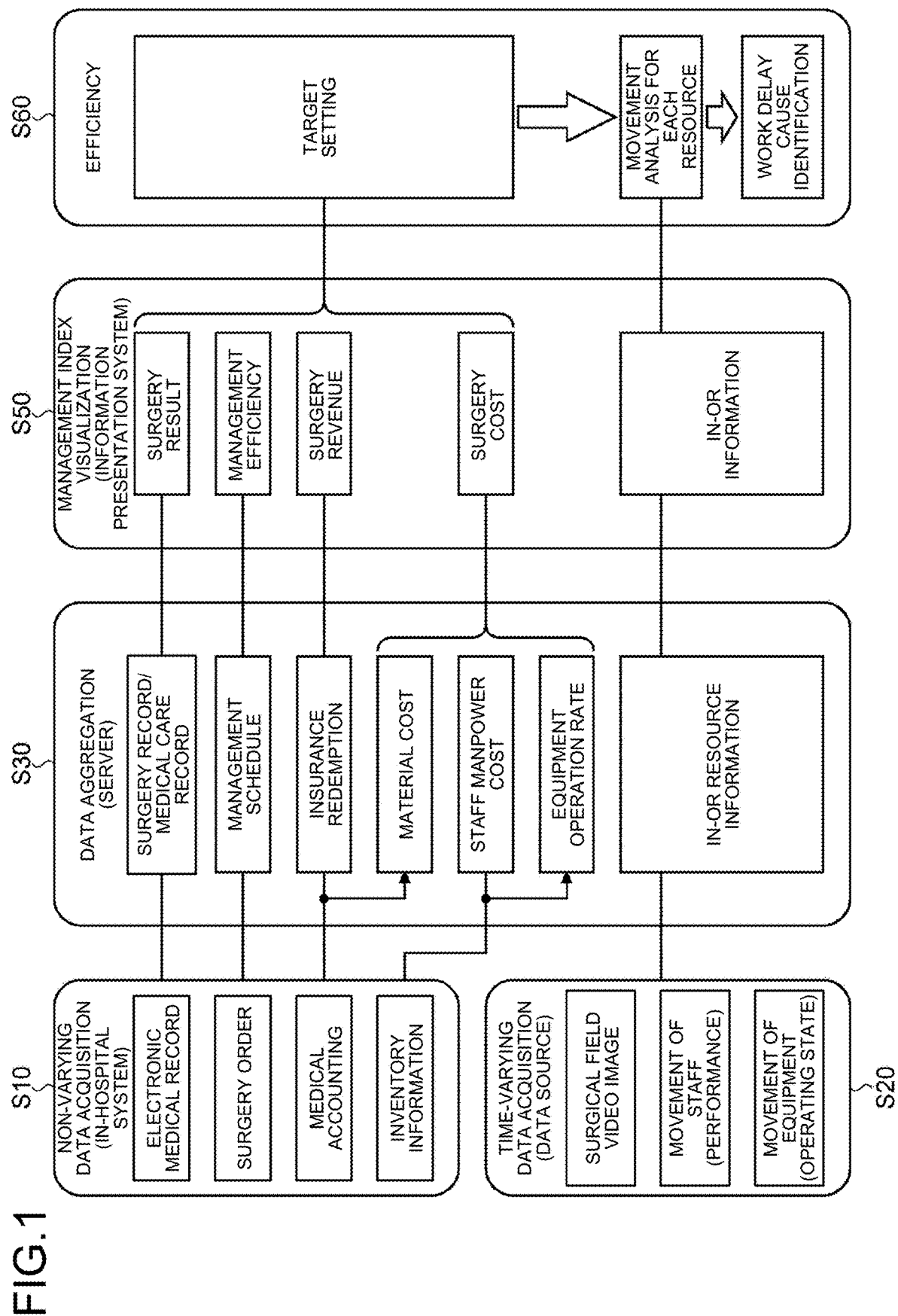
FIG. 1 is a schematic diagram illustrating an efficiency-improving flow of surgery-related service according to a first embodiment.

Hereinafter, embodiment of the present disclosure will be described with reference to the drawings. In the following embodiments, same parts are given the same reference signs to omit redundant description.

Further, the present disclosure will be described according to the following item order.
1. Introduction
2. Embodiment
2.1 Outline of efficiency-improving flow of surgery-related service
2.2 System configuration example
2.3 Example of resource information accumulated in database
2.4 Examples of information presentation screen
2.4.1 Statistical information display screen
2.4.2 Example of surgery-related information presentation screen
2.5 Examples of efficiency-improving flow of surgery-related service
2.5.1 Example of online support flow
2.5.2 Example of offline support flow
2.6 Specific examples of surgery-related information presentation screen
2.6.1 Specific example of data selection area
2.6.2 Specific example of progress display area
2.6.3 Specific example of work content display area
2.6.4 Specific example of resource status display area
2.6.5 Specific example of in-OR video display area
2.6.6 Specific example of resource map display area
2.7 Usage examples of surgery-related information presentation screen
2.7.1 Usage Example 1
2.7.2 Usage Example 2
2.7.3 Usage Example 3
2.7.4 Usage Example 4
2.7.5 Usage Example 5
2.7.6 Usage Example 6
2.7.7 Usage Example 7
2.8 Specific example of information presentation processing unit
2.9 Effects 1. Introduction First, tasks in improving an efficiency of surgery-related service and solutions thereof will be described. Viewpoints to be focused on when improving the efficiency of surgery-related service include viewpoints of management, doctors, workers such as medical staff (hereinafter referred to as staff) and a viewpoint of cases. The management viewpoint is important for identifying a management status of resources including staff and equipment. The staff viewpoint is important for recognizing a scene and supporting a workflow in the surgery-related service including preparation for surgery. The case viewpoint is important for presenting information that will improve quality of treatment to a doctor (hereinafter referred to as a surgeon) and staff who carry out the surgery-related service.

Conventionally, it has not been possible to visualize information based on these viewpoints in an easy-to-understand manner. Therefore, difficulties in finding and identifying problems in the surgery-related service have been disturbing sufficient improvement of the efficiency of the surgery-related service.

The following embodiment enables to further improve the efficiency of the surgery-related service by visualizing the information based on the above viewpoints in a more easily understandable manner.

Specifically, by visualizing the management status of the staff and equipment from various viewpoints, analysis for finding and identifying problems in the surgery-related service is facilitated, thereby supporting creation of an efficient workflow that can reduce cost and time of the surgery-related service. In addition, by providing optimal resources based on the visualized information, it is possible to support further improvement of the workflow efficiency.

2. Embodiment

First, an information processing system and an information processing method and program according to an embodiment of the present disclosure will be described in detail with reference to the drawings.

2.1 Outline of Efficiency-Improving Flow of Surgery-Related Service

FIG. 1 is a schematic diagram illustrating a flow for improving efficiency of the surgery-related service according to the embodiment of the present disclosure. As illustrated in FIG. 1, in the efficiency-improving flow of the surgery-related service according to the present embodiment, Step S10 of acquiring data that does not change with time (hereinafter referred to as non-time-varying data), Step S20 of acquiring data that changes with time (hereinafter referred to as time-varying data), Step S30 of aggregating these pieces of data, Step S50 of providing information based on the aggregated data (hereinafter referred to as surgery-related information) to a user, and Step S60 of increasing efficiency of the workflow of the surgery-related service and resource arrangement by the user based on the surgery-related information provided.

The non-time-varying data acquired in Step S10 is, for example, data registered by the staff including a doctor, a scopist, an anesthesiologist, a nurse, and an accounting clerk in a hospital system (hereinafter referred to as an in-hospital system). The non-time-varying data may include, for example, static data related to an electronic medical record, a surgery order, medical accounting, and inventory information.

The "electronic medical record" may be a medical record in which information regarding medical care performed on a patient to be operated is collected and digitized.

The "surgery order" is, for example, information related to a schedule for each surgery-related service, such as a surgery method, a medical staff and medical team engaged in the surgery (hereinafter, simply referred to as a staff), equipment to be used, in addition to a place of the surgery (hereinafter, also referred to as an operating room (OR)) and a date and time.

The "medical accounting" is, for example, information regarding revenue and expenditure for each surgery-related service. The medical accounting includes, for example, information regarding cost spent for the surgery-related service, an amount billed to a patient, and the insurance redemption amount. Note that the cost spent for the surgery-related service may include manpower cost of doctors and staff engaged in the surgery, cost of medicines and consumables used in the surgery, and a usage fee and depreciation cost of operating room and equipment.

The "inventory information" may be, for example, information regarding inventory and order of equipment, apparatuses, equipment, medicine, and consumables (hereinafter, also referred to as equipment). Note that the medicine may include, for example, an anesthetic and a blood preparation to be used for surgery. In addition, consumables may include gauze and surgical gloves.

The time-varying data acquired in Step S20 is, for example, data acquired from a camera attached to a surgery-related facility such as the operating room, a sensor (hereinafter, also referred to as data source) attached to staff or equipment and may include, for example, a surgical field video image, staff movement (hereinafter, also referred to as performance), and equipment movement (hereinafter, also referred to as an operating state).

The "surgical field video image" may be, for example, video data acquired by the camera disposed in the operating room or a peripheral or related facility thereof.

The "staff movement (performance)" may be, for example, information regarding a motion trace of a position of staff or equipment identified by analyzing the video image acquired by the camera, or the position identified based on a signal from a global positioning system (GPS) oscillator attached to the staff or the device.

The "equipment movement (operating state)" may be, for example, information regarding the operating state of equipment used in the surgery-related service such as an electrocardiogram monitor or an electric scalpel.

In Step S30, the non-time-varying data acquired in Step S10 and the time-varying data acquired in Step S20 are collected and accumulated in a server disposed inside or outside the hospital. Furthermore, in Step S30, a surgery record/medical care record, a management schedule, insurance redemption, a material cost, a staff manpower cost, an equipment operation rate, and in-OR resource information may be derived from the collected data.

The "surgery record/medical care record" may be, for example, a data group in which records of the surgery-related service performed in a hospital identified by the electronic medical record and medical care records are accumulated.

The "management schedule" may be, for example, a data group regarding a schedule of a surgery-related facility, equipment, and staff planned according to the surgery order.

The "insurance redemption" may be, for example, a data group regarding an insurance redemption amount for each surgery-related service or medical care identified based on the medical accounting.

The "material cost" may be, for example, a data group regarding the manpower cost of each staff, running cost caused by using equipment, and unit price of consumable identified based on the surgery order.

The "equipment operation rate" may be, for example, a data group regarding an operation rate of equipment used in the surgery-related service identified based on the surgery order.

The "in-OR resource information" may be, for example, a data group in which information regarding resources such as staff and equipment identified from the time-varying data.

In Step S50, for example, a surgery result, a management efficiency, a surgery revenue, a surgery cost, and in-OR information are visualized and presented to the user according to the data groups aggregated in the server in Step S30.

The "surgery result" may be, for example, visualized information, for each surgeon and staff, on evaluation of work or a result of the surgery-related service each surgeon or staff that visualizes.

The "management efficiency" may be, for example, visualized information on a degree of efficiency of the management of resources including the surgeon, the staff, and the equipment.

The "surgery revenue" may be, for example, visualized information on revenue and expenditure in the surgery-related service.

The "surgery cost" may be, for example, visualized information on running cost including manpower cost and material costs required for the surgery related service.

The "in-OR information" may be, for example, visualized information on "in-OR resource information" and visualized information on an analysis result of the "in-OR resource information".

In Step S60, for example, the user sets an item to be targeted for improving the efficiency based on the information including the surgery result, management efficiency, surgery revenue, and surgery cost visualized in Step S50. Then, the user analyzes movement of each resource in the targeted item based on the visualized in-OR information, and identifies a cause of work delay, thereby improving the efficiency of the surgery-related service.

2.2 System Configuration Example

Figure 2:
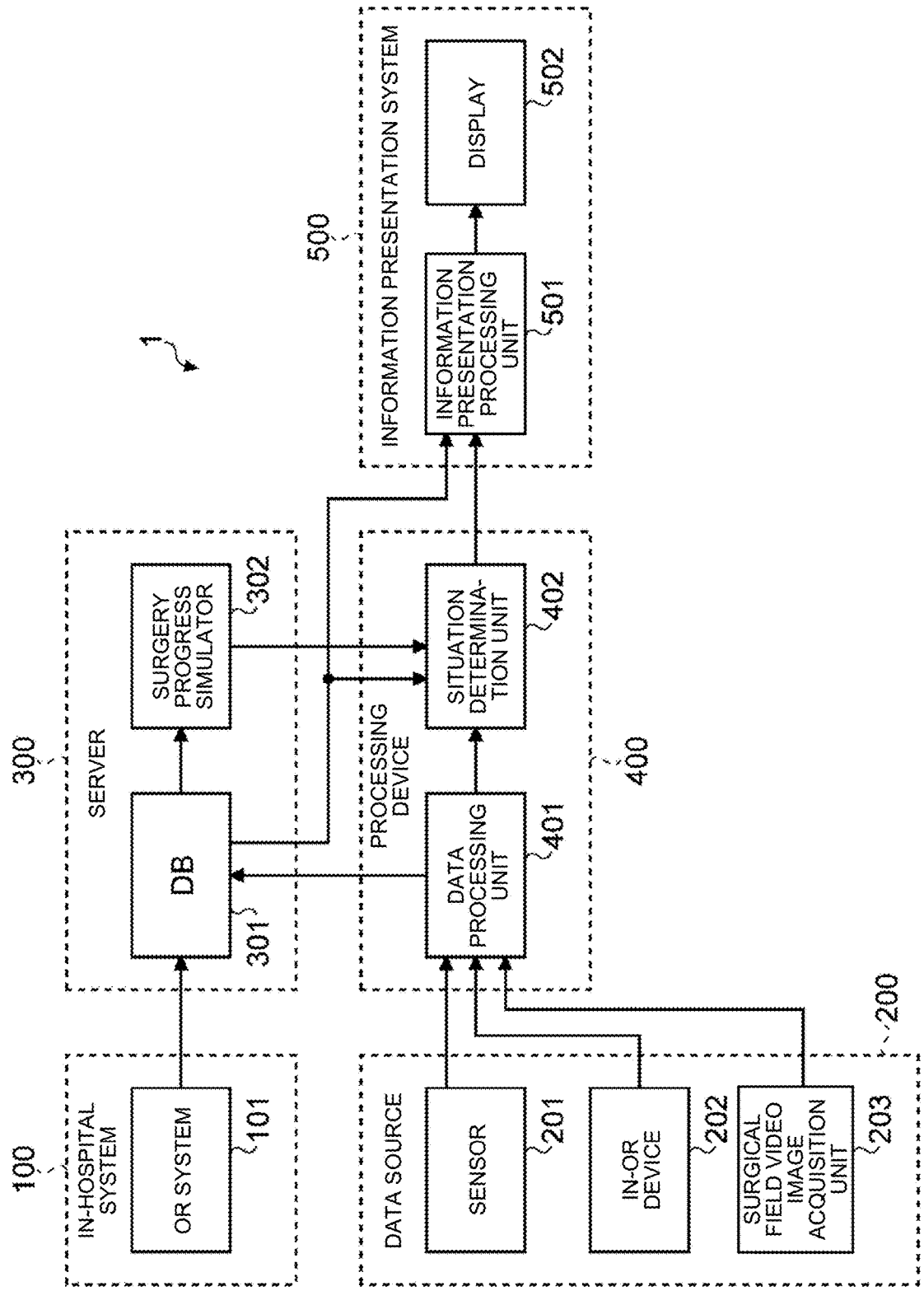
FIG. 2 is a block diagram illustrating a schematic configuration example of an information processing system according to an embodiment of the present disclosure.

FIG. 2 is a block diagram illustrating a schematic configuration example of an information processing system according to the present embodiment. As illustrated in FIG. 2, an information processing system 1 according to the present embodiment includes an in-hospital system 100, a data source 200, a server 300, a processing device 400, and an information presentation system 500. The data source 200, the server 300, the processing device 400, and the information presentation system 500 may be communicably connected to each other via a predetermined network such as a local area network (LAN), a wide area network (WAN), the Internet, or a mobile communication network.

The in-hospital system 100 includes, for example, an operating room system (hereinafter referred to as an OR system.) 101 installed in a medical facility such as a hospital or a clinic, and may be a system that executes registration and management of the non-time-varying data such as the electronic medical record, the surgery order, the medical accounting, and the inventory information. Note that the medical facility is not necessarily a facility installed in one site, and may be a facility arranged in a plurality of sites in a distributed manner.

The data source 200 includes, for example, a sensor 201 such as a GPS transmitter and a radio frequency identifier (RFID) tag, an in-OR device 202 such as the electrocardiogram monitor and the electric scalpel, and a surgical field video image acquisition unit 203 such as a camera, and acquires the time-varying data such as the surgical field video image, the staff movement, and the equipment movement. Note that the sensor 201, the in-OR device 202, and the surgical field video image acquisition unit 203 may be arranged in the medical facility in which the in-hospital system 100 is installed or in a doctor and staff working in the medical facility.

The server 300 includes, for example, a database 301 and a surgery progress simulator 302. The database 301 collects and accumulates, for example, the non-time-varying data registered in the in-hospital system 100 and the time-varying data acquired by the data source 200. For example, the surgery progress simulator 302 uses the data accumulated in the database 301 to execute reproduction, analysis, and simulation of a flow of entire surgery (entire process), work content in each process and each work section in each process in the entire surgery, instruments used in each work section, and movement of equipment and staff in each work section.

In the present description, the "process (excluding the entire process)" may be a section (also referred to as a first section) obtained by dividing the entire process of surgery into processes according to work content, and the work section may be a section (also referred to as a second section) obtained by further dividing each process into work contents.

The processing device 400 includes, for example, a data processing unit 401 and a situation determination unit 402. The data processing unit 401 converts, for example, the time-varying data acquired by the data source 200 into a necessary format. The time-varying data subjected to format conversion is transmitted to the database 301 and accumulated, for example, and is input to the situation determination unit 402 as necessary. The situation determination unit 402 determines, for example, a situation at a certain time point of currently ongoing surgery and past surgery based on the contents and results of reproduction, analysis, and simulation input from the surgery progress simulator 302 and the time-varying data input from the data processing unit 401.

The information presentation system 500 includes, for example, an information presentation processing unit 501 and a display 502. The information presentation processing unit 501 generates data for displaying and reproducing contents, results, and situation determination results of reproduction, analysis, and simulation of the flow of the entire surgery, work content in each work section, instruments used in each work section, and movement of equipment and staff in each work section (surgery-related information) input from the situation determination unit 402 in a manner easy for the user to recognize. The display 502 presents the above contents, results, and situation determination results to the user by displaying and reproducing the data generated by the information presentation processing unit 501.

Note that the "manner easy for the user to recognize" in the present description may be, for example, an image, sound, or vibration. Furthermore, "visualization" in the present description may include audio and tactile recognition, in addition to visual recognition.

2.3 Example of Resource Information Accumulated in Database

Now, an example of information on resources (referred to as resource information) accumulated in the database 301 of the server 300 will be described. In the present description, the resources may be a person, an object, and a facility involved in the surgery-related service.

FIG. 3 is a schematic diagram illustrating an example of the resource information accumulated in the database according to the present embodiment. As illustrated in FIG. 3, for example, "resource status and quantified value" and "conversation content and environmental sound" may be accumulated in the database 301 as OR management resource information 311.

For example, when the resource is a person, such as the surgeon or the staff, the "resource status and quantified value" may include the number of staffs, the number of times of OR entry/exit of each staff, a main work place (heat map) for each staff, and a movement amount (number of steps, moving speed, etc.) for each staff. Note that, also in a case where the resource is an object such as equipment, quantified values can be accumulated similarly.

The "conversation content and environmental sound" may include, for example, the number of instructions to the staff, recording of various "values", and equipment operation sound. Note that the recording of "values" may include recording of a count value of supplies such as gauze and recording of time information such as an elapsed time from the start of surgery. In addition, the equipment operation sound can be used to identify the operation timing of each piece of equipment.

Furthermore, in the database 301, for example, information regarding a surgeon, a scopist, an anesthesiologist, a nurse, and OR equipment and apparatus may be accumulated as the resource specific information 312.

The information specific to the "surgeon" may include, for example, number of times of replacement of surgical tools (may include types of surgical tools), number of times of in-OR movement in and disengagements from the OR site, and time until accomplishing a small work.

The information specific to the "scopist" may include, for example, information on work content (both hands, single hand, operation frequency, etc.), time from an instruction to accomplishment, and the number of times of cleaning.

The information specific to the "anesthesiologist" may include, for example, information on the number of work trials (tracheal intubation, etc.), terminal operation time (information input time), and work time related to anesthesia application.

The information specific to the "nurse" may include, for example, information on time related to equipment movement and preparation, gauze counts, terminal operation time, and an affected part (in particular, before and after surgery), and time required.

The information specific to the "OR facility/equipment" may include, for example, information on a change in posture, a change in bed inclination, an endoscope image output time, use time of a diagnosis device (ultrasonic wave, etc.), number of times of turning on/off equipment, timing (electric scalpel, etc.), change in a setting value (what is set to which value, etc.), and anesthesia apparatus related information (terminal input information, vital data).

2.4 Examples of Information Presentation Screen

Next, in the present exemplary embodiment, an information presentation screen presented on the display 502 of the information presentation system 500 will be described with reference to an example. Note that the information presentation screen described below may be generated by any of the surgery progress simulator 302, the situation determination unit 402, and the information presentation processing unit 501.

2.4.1 Statistical Information Display Screen

Figure 4:
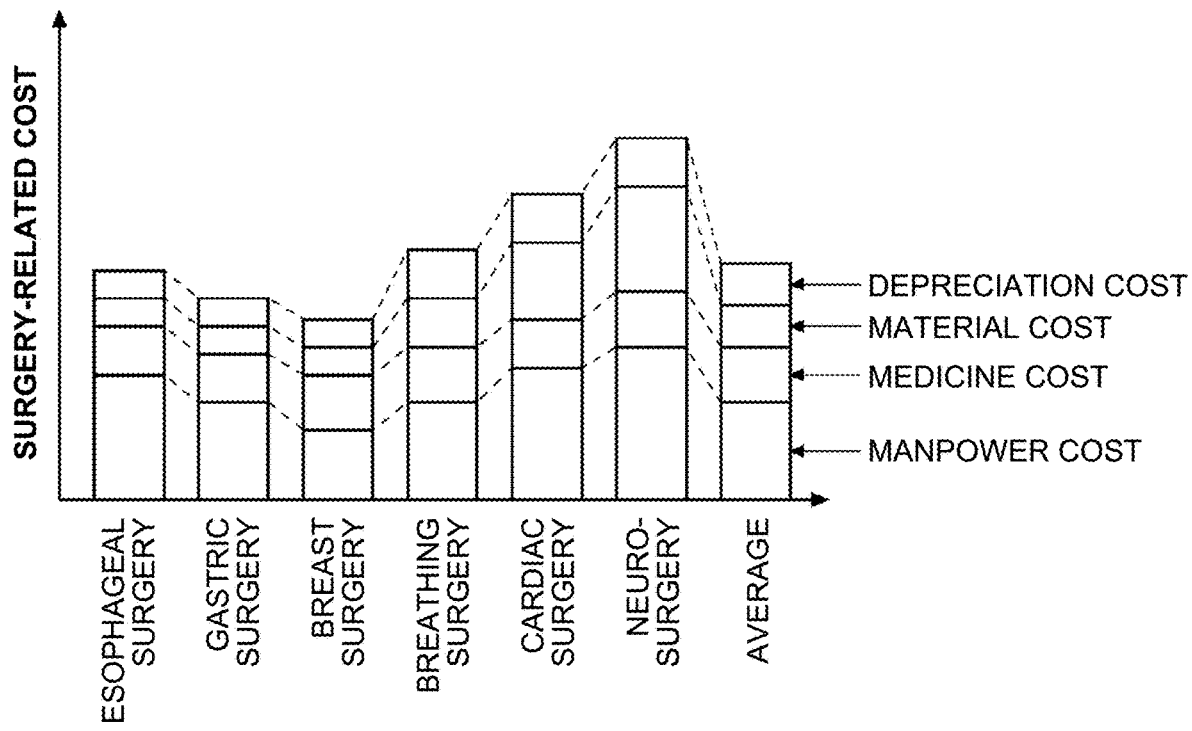
FIG. 4 is a graph illustrating an example of a statistical information display screen according to the embodiment of the present disclosure.
Figure 5:
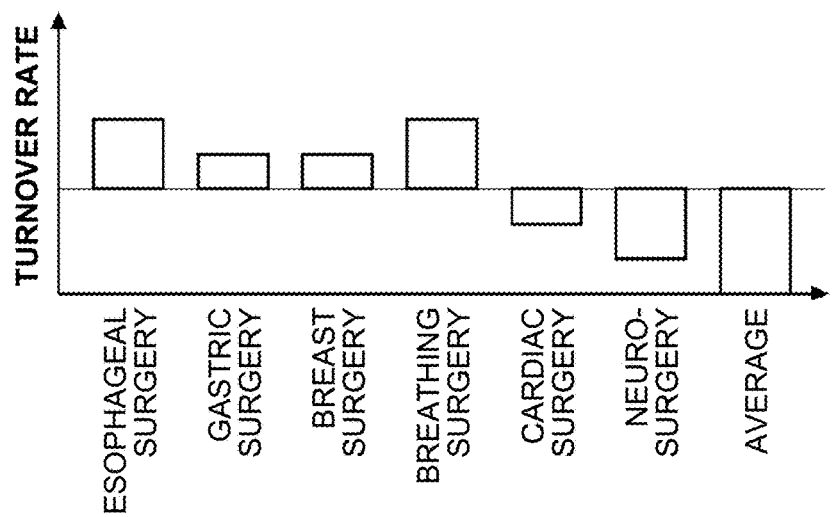
FIG. 5 is a graph illustrating another example of the statistical information display screen according to the embodiment of the present disclosure.

FIG. 4 and FIG. 5 are graphs illustrating an example of a statistical information display screen according to the present embodiment. The statistical information display screen illustrated in FIG. 4 and FIG. 5 is displayed on the display 502, for example, when the user executes "target setting" in Step S60 in FIG. 1.

First, as illustrated in FIG. 4, on the first statistical information display screen, for example, statistical information on "manpower cost", "medicine cost", "material cost", and "depreciation cost" is collectively displayed for each surgery type in charge of the surgery-related service, such as "esophagus surgery", "stomach surgery", "mammary gland surgery", "respiratory surgery", "cardiac surgery", and "neurosurgery". Note that the first statistical information display screen may display an average cost of all surgery types for reference.

In addition, as illustrated in FIG. 5, on the second statistical information display screen, for example, statistical information on a turnover rate of the surgery-related facility is collectively displayed for each surgery type in charge of the surgery-related service. Note that the turnover rate may be, for example, a ratio of time filled with an actual surgery schedule when a state in which the surgery schedule is filled without vacant time is set to "1 (=100%)".

In Step S60 in FIG. 1, for example, the user views and examines the first and/or second statistical information display screen, so that it is possible to identify which surgery-related service is not efficient, and to set an efficiency improvement target.

Note that the statistical information display screens illustrated in FIG. 4 and FIG. 5 are merely examples, and a screen may be appropriately added or changed according to a task type or item that the hospital focuses on. In addition, the first statistical information display screen and the second statistical information display screen do not need to be displayed on separate screens, and may be displayed on the same screen.

2.4.2 Example of Surgery-Related Information Presentation Screen

Figure 6:
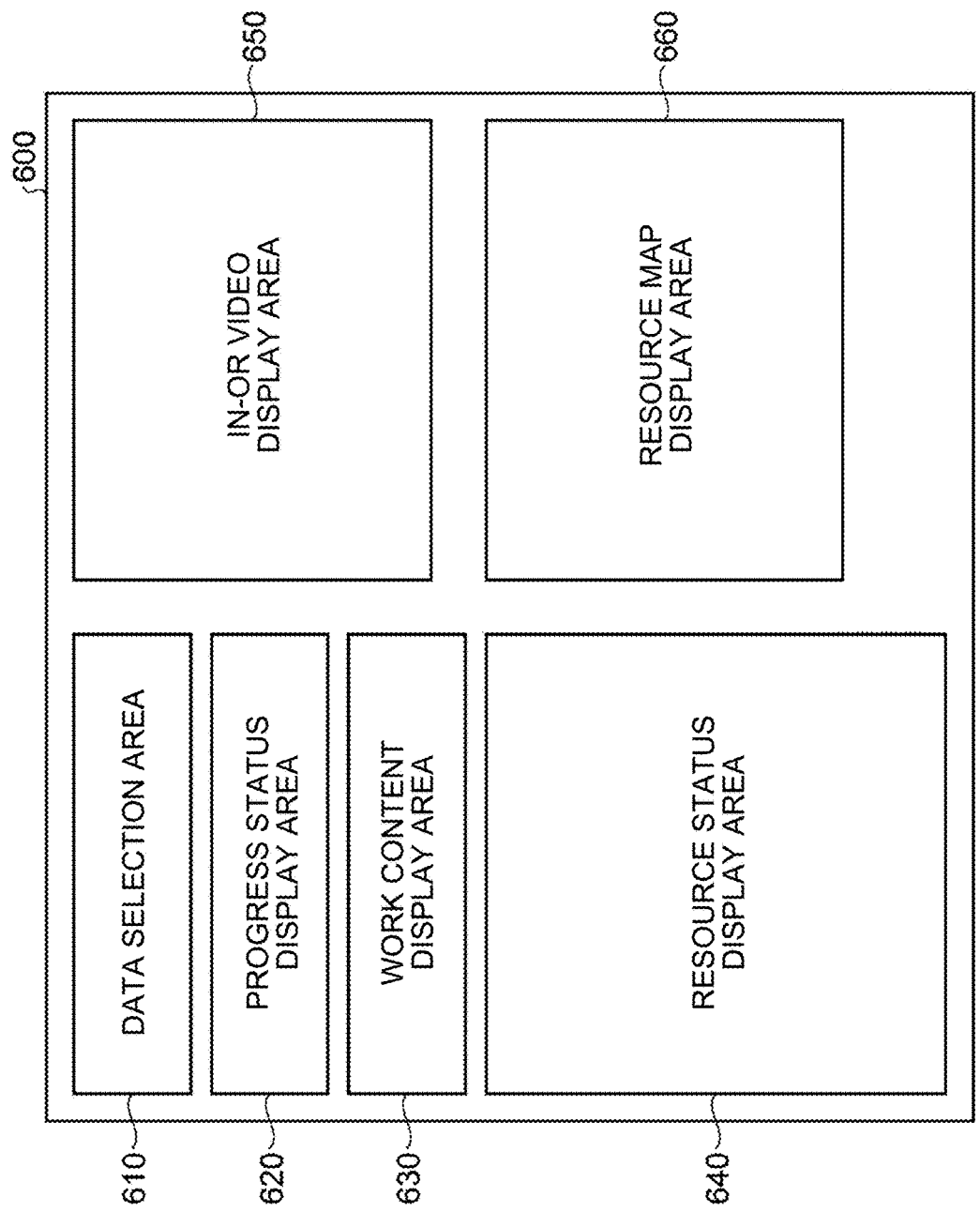
FIG. 6 is a diagram illustrating an example of a surgery-related information presentation screen according to the embodiment of the present disclosure.

FIG. 6 is a diagram illustrating an example of a surgery-related information presentation screen according to the present embodiment. The surgery-related information presentation screen illustrated in FIG. 6 is displayed on the display 502 when, for example, the user performs "movement analysis for each resource" or "work delay cause identification" in Step S60 in FIG. 1.

As illustrated in FIG. 6, the surgery-related information presentation screen 600 includes a data selection area 610, a progress status display area 620, a work content display area 630, a resource status display area 640, an in-OR video display area 650, and a resource map display area 660.

Note that, in view of the fact that treatment and surgery are managed for each case of a patient in a general hospital, the following description gives an example of grouping data for each case.

The data selection area 610 is, for example, an area for setting case data of a case to be analyzed and case data used as a reference for comparing with and examining the case data (hereinafter referred to as reference data). Note that the case data may be case data regarding currently ongoing surgery, or may be case data regarding past surgery accumulated in the database 301. Furthermore, the reference data is case data regarding surgery different from the case data and is case data regarding past surgery accumulated in the database 301, or may be case data obtained by statistics or equalization of case data of the same case type or that adopting the same surgical method in the past surgeries.

The progress status display area 620 is an area indicating the entire surgery process and a progress of the entire surgery process, and may be, for example, an area for displaying an entire flow of one surgery (hereinafter referred to as an entire scene). In the present description, the progress status display area 620 is also referred to as a surgery process area.

The work content display area 630 is an area indicating work content and a progress of the work content in a part of the entire process, and may be, for example, an area for displaying details of the work content in one of the work sections displayed in the progress status display area 620. In the present description, the work content display area 630 is also referred to as a work process area.

The resource status display area 640 is also referred to as a resource display area, and may be, for example, an area for displaying the status of resources such as the surgeon, the staff, and the equipment in the work section selected in the progress status display area 620. The resource status display area 640 is preferably arranged in an area arranged further adjacent to the layout of the progress status display area 620 and the work content display area 630. Note that the "resource status" may be, for example, a status whether or not a person such as the surgeon or the staff is in the operating room or whether or not the person is ready to start working. For example, in the case of equipment such as the electrocardiogram monitor or the electric scalpel, the "resource status" may be a status whether or not the equipment is normally activated or whether or not the equipment is in use or in standby. Furthermore, the display content and type of resource displayed in the resource status display area 640 may be configured to be changeable as appropriate by the user.

The in-OR video display area 650 is also referred to as a video area, and may be, for example, an area for reproducing the surgical field video image acquired as the time-varying data by the surgical field video image acquisition unit 203 of the data source 200.

The resource map display area 660 is also referred to as a resource map area, and may be, for example, an area for displaying positions of resources such as the surgeon, the staff, and the equipment on a two-dimensional map representing the operating room or the surgery-related facility including the operating room.

Note that, for example, the status of each resource displayed in the resource status display area 640 and the position of the resource displayed on the two-dimensional map may change to match the surgical field video image reproduced in the in-OR video display area 650. In the progress status display area 620 and the work content display area 630, a position on a time axis of the surgical field video image reproduced in the in-OR video display area 650 may be displayed by graphics such as color and bar.

2.5 Examples of Efficiency-Improving Flow of Surgery-Related Service

Next, an efficiency-improving of the surgery-related service according to the present embodiment will be described with reference to an example. The efficiency-improving of surgery-related service according to the present embodiment includes a flow that supports real-time analysis for the user (hereinafter referred to as an online support flow) and a flow that supports analysis after surgery based on the case data accumulated in the database 301 (hereinafter referred to as an offline support flow).

2.5.1 Example of Online Support Flow

Figure 7:
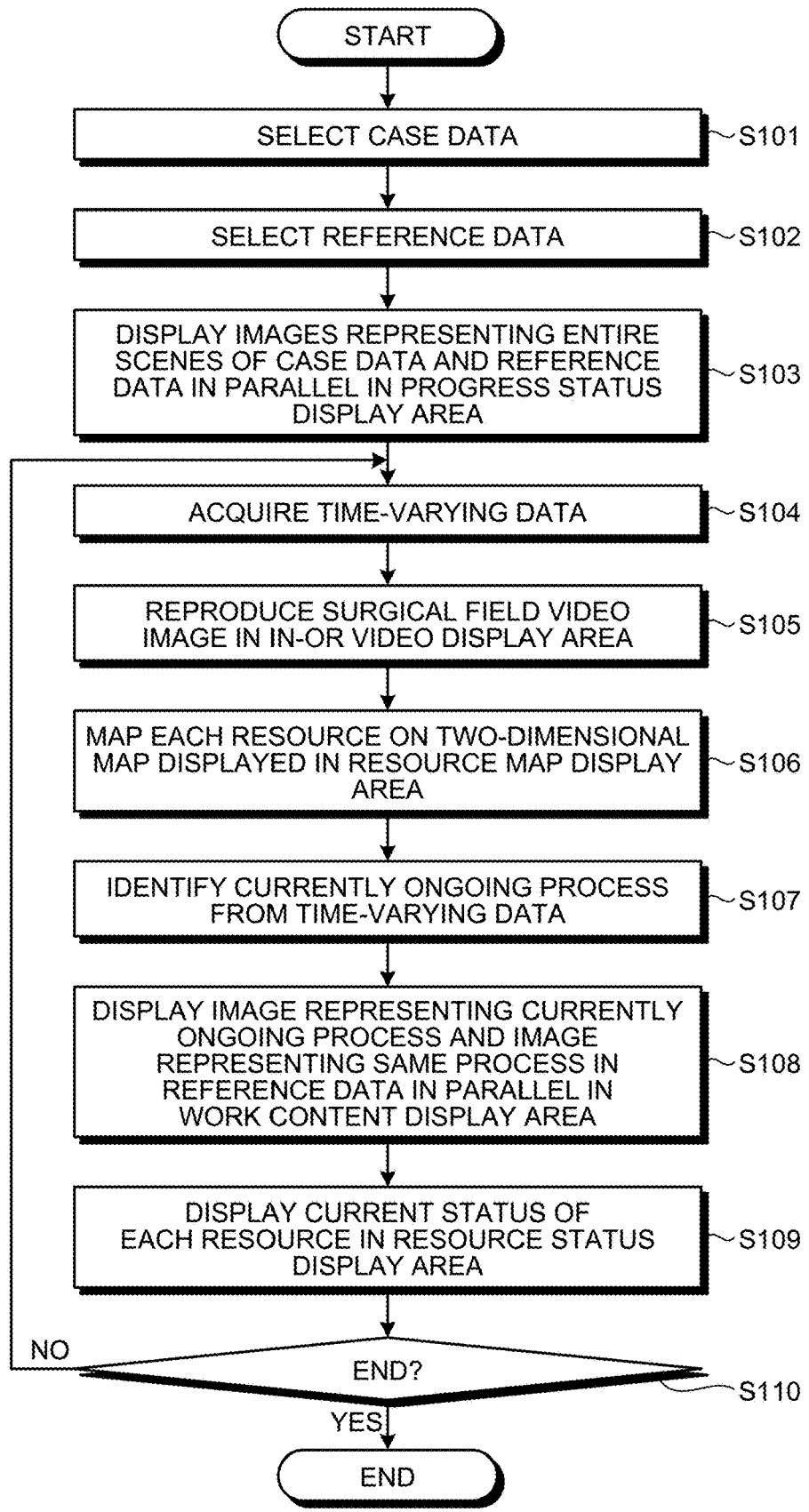
FIG. 7 is a flowchart illustrating an example of an online support flow according to the embodiment of the present disclosure.

FIG. 7 is a flowchart illustrating an example of the online support flow according to the present embodiment. Note that, in the online support flow illustrated in FIG. 7, it is assumed that the surgery-related information presentation screen 600 is first displayed on the display 502. In the following description, the operation of the information presentation processing unit 501 will mainly be described.

In the online support flow, first, at the start of surgery, for example, the user operates and selects a menu displayed in the data selection area 610 of the surgery-related information presentation screen 600 displayed on the display 502, thereby selecting case data registered in advance regarding surgery to be performed (Step S101). Then, the information presentation processing unit 501 reads the selected case data from the database 301. Note that the selected case data may be a data set including non-time-varying data registered in advance. The case data read from the database 301 may also be input to the situation determination unit 402.

Subsequently, the user operates and selects the menu displayed in the data selection area 610 of the surgery-related information presentation screen 600 also displayed on the display 502, thereby selecting one of the reference data accumulated in the database 301 (Step S102). Then, the information presentation processing unit 501 reads the selected reference data from the database 301.

When the case data and the reference data are selected in this manner, the information presentation processing unit 501 generates an image representing the entire scene of each of the case data and the reference data. These images are displayed, for example, in parallel in the vertical direction in the progress status display area 620 of the surgery-related information presentation screen 600 displayed on the display 502 (Step S103).

Thereafter, when the surgery starts and various pieces of time-varying data are acquired by the data source 200, the information presentation processing unit 501 sequentially acquires the time-varying data along a time series from the processing device 400 (Step S104).

Next, the information presentation processing unit 501 reproduces the surgical field video image in the acquired time-varying data in the in-OR video display area 650 of the surgery-related information presentation screen 600 displayed on the display 502 (Step S105).

Subsequently, the information presentation processing unit 501 maps and displays resources such as the surgeon, the staff, and the equipment in the resource map display area 660 of the surgery-related information presentation screen 600 displayed on the display 502 according to the movement of the staff and the movement of the equipment in the time-varying data acquired (Step S106).

In addition, the situation determination unit 402 in the processing device 400 identifies a currently ongoing work section in the entire scene based on the time-varying data acquired by the data source 200 and input via the data processing unit 401 and the case data input from the database 301 (Step S107). Note that the information presentation processing unit 501 is notified of the identified work section.

The information presentation processing unit 501 generates an image representing the work section in the case data and an image representing the work section in the reference data based on the currently ongoing work section notification of which is provided, and displays the images, for example, in parallel in the vertical direction in the work content display area 630 of the surgery-related information presentation screen 600 displayed on the display 502 (Step S108).

Furthermore, according to the acquired time-varying data, the information presentation processing unit 501 displays the current status of resources such as the surgeon, the staff, and the equipment in a list form in the resource status display area 640 of the surgery-related information presentation screen 600 displayed on the display 502 (Step S109).

Then, the information presentation processing unit 501 determines whether or not to end the present operation (Step 5110). To end the present operation (YES in Step 5110), the information presentation processing unit 501 ends the present operation. On the other hand, to continue (NO in Step 5110), the information presentation processing unit 501 returns to Step S104 and executes operations in Step S104 and subsequent steps.

By operating as described above, it is possible to visualize information such as the surgical field video image of the currently ongoing surgery and the position and status of the resources in real time and present the visualized information to the user. Thus, it is possible to give an appropriate instruction to the currently ongoing surgery. As a result, it is possible to further improve the efficiency of the surgery-related service.

2.5.2 Example of Offline Support Flow

Figure 8:
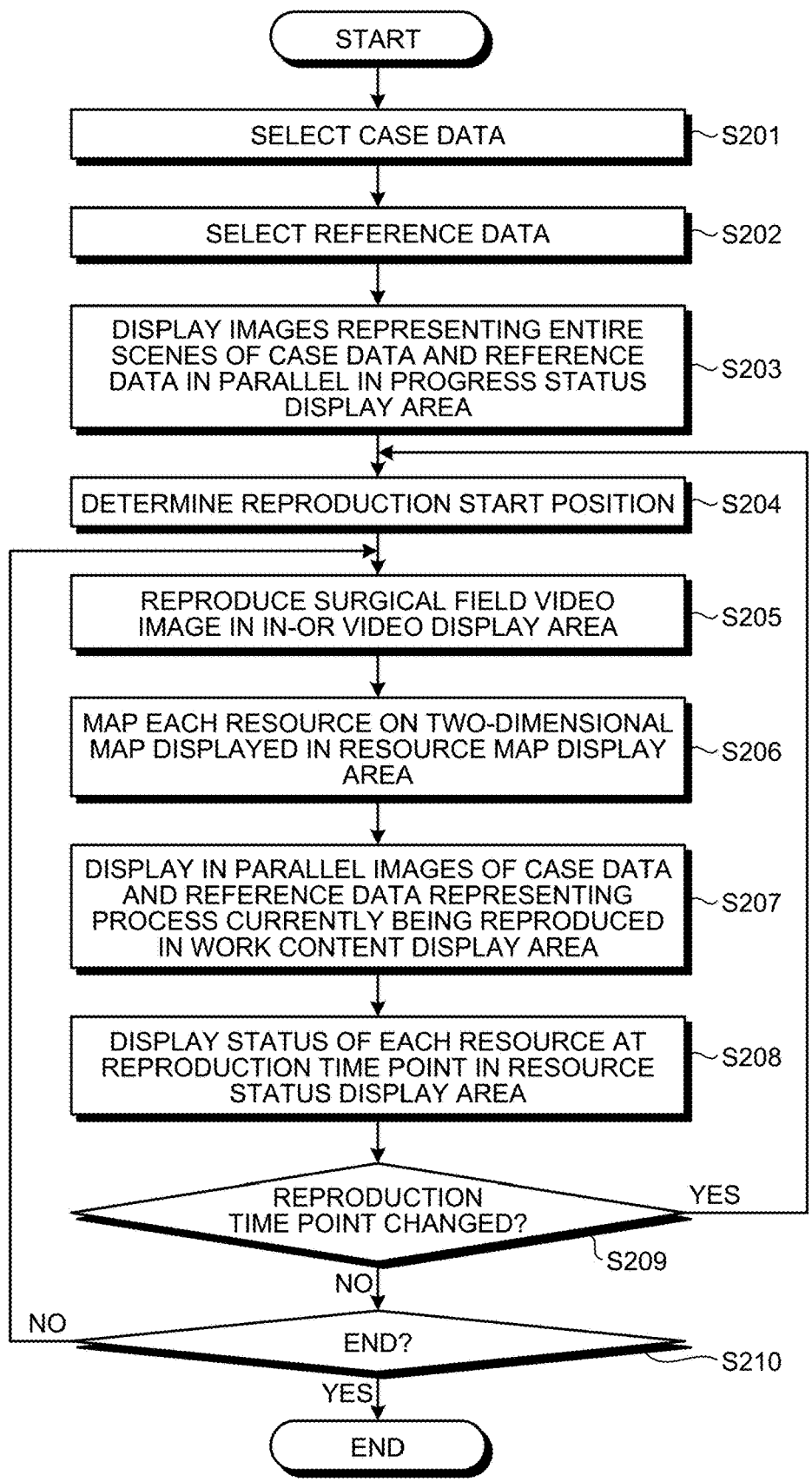
FIG. 8 is a flowchart illustrating an example of an offline support flow according to the embodiment of the present disclosure.

FIG. 8 is a flowchart illustrating an example of an offline support flow according to the present embodiment. Note that, in the offline support flow illustrated in FIG. 8, it is assumed that the surgery-related information presentation screen 600 is first displayed on the display 502. In the following description, the operation of the information presentation processing unit 501 will mainly be described.

In the offline support flow, first, at the start of surgery, for example, the user operates and selects the menu displayed in the data selection area 610 of the surgery-related information presentation screen 600 displayed on the display 502, thereby selecting case data performed in advance and registered in the database 301 (Step S201). Then, the information presentation processing unit 501 reads the selected case data from the database 301. The case data read from the database 301 may also be input to the situation determination unit 402.

Subsequently, the user operates and selects the menu displayed in the data selection area 610 of the surgery-related information presentation screen 600 also displayed on the display 502, thereby selecting one of the reference data accumulated in the database 301 (Step S202). Then, the information presentation processing unit 501 reads the selected reference data from the database 301.

When the case data and the reference data are selected in this manner, the information presentation processing unit 501 generates an image representing the entire scene of each of the case data and the reference data, and displays these images in the progress status display area 620 of the surgery-related information presentation screen 600 displayed on the display 502, for example, in parallel in the vertical direction (Step S203).

Next, the information presentation processing unit 501 determines a reproduction start position in the case data (Step S204). When it is immediately after the case data is read, the reproduction start position determined in Step S204 may be a head of the case data, which is time series data. Furthermore, in a case where a reproduction time point is changed by the user in Step S209 described later, the position on the time series designated at that time may be set as the reproduction start position (in this case, also referred to as a reproduction restart position). Note that the reproduction time point may be a position on a time axis at which reproduction is currently performed.

Next, the information presentation processing unit 501 reproduces, from the determined reproduction start position, the surgical field video image in the acquired time-varying data in the in-OR video display area 650 of the surgery-related information presentation screen 600 displayed on the display 502 (Step S205).

Subsequently, the information presentation processing unit 501 maps and displays the resources of the surgeon, the staff, and the equipment in the resource map display area 660 of the surgery-related information presentation screen 600 displayed on the display 502 according to the movement of the staff and the movement of the equipment at the reproduction time point in the acquired time-varying data (Step S206).

In addition, the information presentation processing unit 501 generates an image representing the work section at the reproduction time point in the case data and an image representing the work section at the reproduction time point in the reference data, and displays the images, for example, in parallel in the vertical direction in the work content display area 630 of the surgery-related information presentation screen 600 displayed on the display 502 (Step S207).

Furthermore, the information presentation processing unit 501 displays, according to the acquired time-varying data, the status at the reproduction time point of the resources such as the surgeon, staff, and equipment in a list form in the resource status display area 640 of the surgery-related information presentation screen 600 displayed on the display 502 (Step S208).

Next, for example, the information presentation processing unit 501 determines whether or not the instruction to change the reproduction time point is given by the user moving the slider displayed in the progress status display area 620 or the work content display area 630 (Step S209). When the instruction is not changed (NO in Step S209), the process proceeds to Step S210. On the other hand, when the reproduction time point is changed (YES in Step S209), the information presentation processing unit 501 returns to Step S204 and executes reproduction from the changed reproduction time point by executing processes in Step S204 and subsequent steps In Step S210, the information presentation processing unit 501 determines whether or not to end the present operation. To end the present operation (YES in Step S210), the information presentation processing unit 501 ends the present operation. On the other hand, to continue (NO in Step S210), the information presentation processing unit 501 returns to Step S205 and executes operations in Step S205 and subsequent steps.

By operating as described above, it is possible to visualize and present to the user information such as the surgical field video image of the surgery performed in the past and the position and status of the resource, and thus, it is possible to easily analyze the surgery performed in the past. As a result, it is possible to further improve the efficiency of the surgery-related service.

2.6 Specific Examples of Surgery-Related Information Presentation Screen

Next, a specific example of the surgery-related information presentation screen according to the present embodiment will be described in detail below with reference to the drawings.

Figure 9:
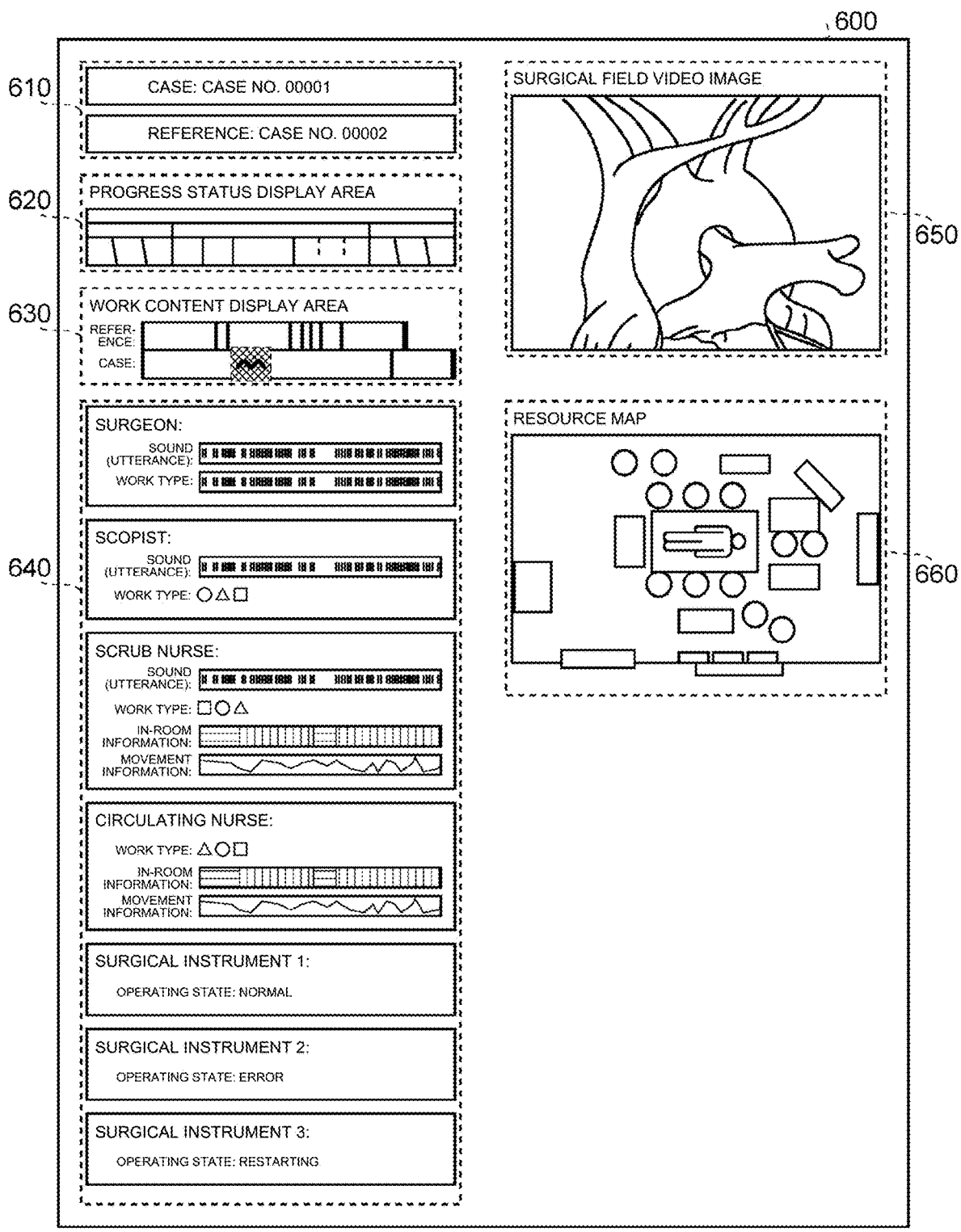
FIG. 9 is a screen view illustrating a specific example of the surgery-related information presentation screen according to the embodiment of the present disclosure.

FIG. 9 is a screen view illustrating a specific example of the surgery-related information presentation screen according to the present embodiment. Note that the surgery-related information presentation screen illustrated in FIG. 9 may be displayed entirely in one screen, or may be partially displayed in the screen and scrolled to view the entire screen.

2.6.1 Specific Example of Data Selection Area

As illustrated in FIG. 9, in the data selection area 610, for example, a file name or an identification number of the case data set as an analysis target and the file name or the identification number of the reference data set as a comparison target are displayed in parallel in the vertical direction. In the example illustrated in FIG. 9, case data No. 00001 is selected as the analysis target and reference data No. 00002 is selected as the comparison target.

As a method of setting each of the case data and the reference data, for example, various methods may be adopted, including a method in which selectable case data or reference data are listed in a pull-down menu and the user selects the case data or the reference data from the list, and a method in which the user sets the case data or the reference data by inputting the file name or the identification number of the case data or the reference data.

2.6.2 Specific Example of Progress Display Area

A specific example of the progress status display area 620 will be described with reference to FIG. 10. FIG. 10 is a diagram illustrating the specific example of the progress status display area according to the present embodiment. As illustrated in FIG. 10, in the progress status display area 620, for example, the entire scene of the selected case data is displayed as a belt-like overall image 621 with the horizontal axis as the time axis. Here, for example, the belt-like overall image 621 may be divided by a dividing line 622 for each work section constituting the entire scene. Each work section divided by the dividing line 622 may be defined as an area selectable by the user.

In each work section, for example, a time ratio with respect to the corresponding work section in the reference data may be displayed. Alternatively, the work section that has taken a longer time than the corresponding work section in the reference data may be highlighted. Highlighting according to the present embodiment may include, for example, display with a highlight color such as red, display with a thick frame or a bold line, highlighted display, and display by sorting on the list. For example, for "preliminary preparation" that has taken longer time than the reference data, "(102%)" that is a time ratio with respect to "preparation" in the reference data may be indicated, and a character string indicating "preparation (102%)" or the area may be highlighted in red.

In this way, by adopting a display pattern that can easily and visually identify a work section that has required a longer time than the corresponding work section in the reference data, it is possible to easily identify a work section in which a delay has occurred or a work section that is not efficient.

Note that the setting of the dividing line 622 of each work section in the entire scene may be automatically executed in the server 300 according to the surgical field video image and the time-varying data such as the staff movement and the equipment movement, or may be manually set by the user. In this case, when the analysis information of the case is insufficient and it is not possible to distinguish between consecutive two work sections (for example, a gallbladder cutting step and a cholecystectomy step), a plurality of work sections may be combined and displayed as one work section, such as "gallbladder cutting: cholecystectomy" in FIG. 11.

2.6.3 Specific Example of Work Content Display Area

Returning to FIG. 9 for the description, in the work content display area 630, for example, details of the work content in the work section selected by the user from the work sections displayed in the progress status display area 620 may be arranged and displayed in parallel with the progress status display area 620. A specific example of the work content display area 630 will be described with reference to FIG. 11.

Figure 11:
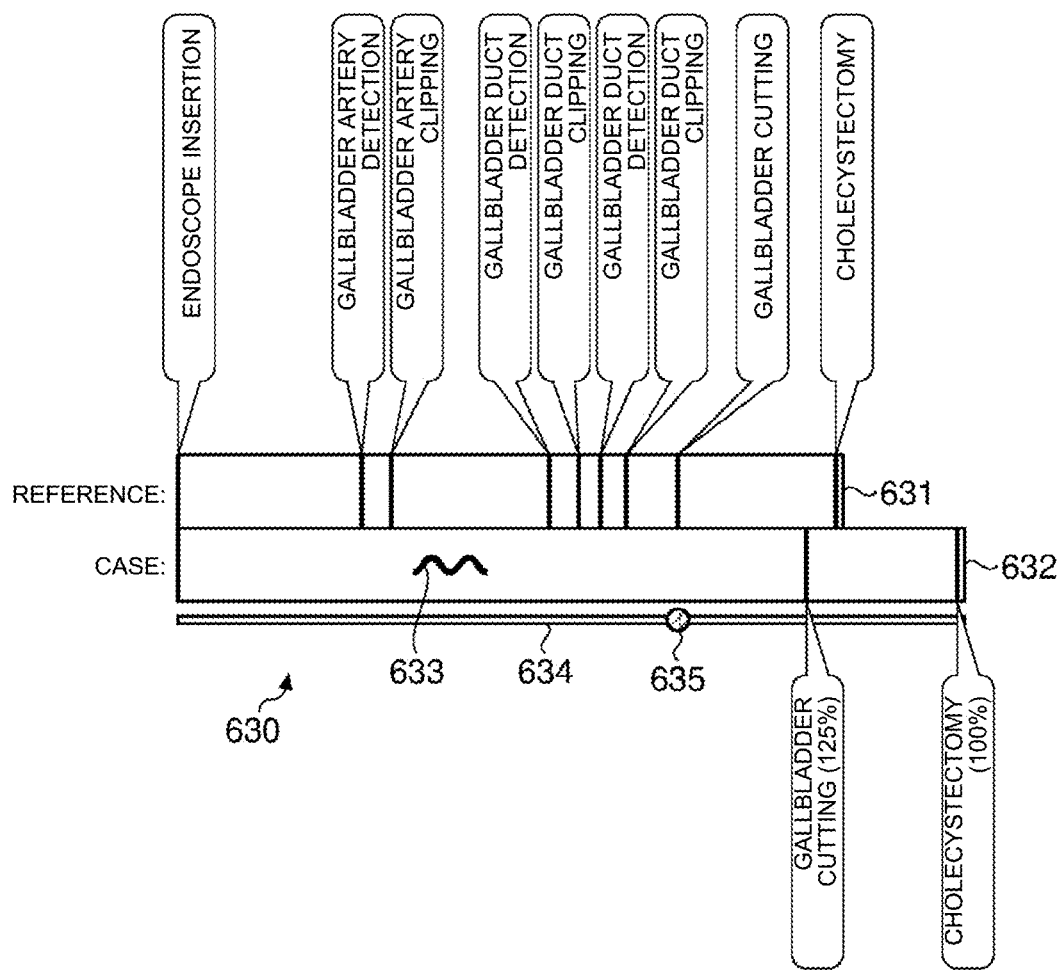
FIG. 11 is a diagram illustrating a specific example of a work content display area according to the embodiment of the present disclosure.

FIG. 11 is a diagram illustrating a specific example of the work content display area according to the present embodiment. As illustrated in FIG. 11, in the work content display area 630, for example, the detailed work content of each of the case data and the reference data in the work section (hereinafter also referred to as a focused section.) selected by the user in the progress status display area 620 is displayed as belt-like section images 631 and 632 with the horizontal axis as the time axis.

For example, the section image 631 of the case data and the section image 632 of the reference data may be arranged in parallel in the vertical direction. As described above, by arranging the section image 631 of the case data and the section image 632 of the reference data in parallel, it is possible to visually and easily recognize how much delay has occurred in the analyzed surgery.

As illustrated in FIG. 11, the details of the work content may be tagged in the form of a balloon with respect to the position where the work is executed in the section images 631 and 632, or may be tagged inside the section images 631 and 632. In this manner, by tagging each of the section image 631 of the case data and the section image 632 of the reference data with detailed work contents, it is possible to visually and easily recognize which work content has delayed.

Furthermore, for example, in the section image 631 of the case data, a mark 633 may be provided to clearly indicate a period with no movement in the surgical field video image for a long time, or a period with no movement of the staff or the equipment for a long time. As the mark 633, various forms capable of clearly indicating the corresponding period, such as a red jagged line for calling attention, may be adopted. This makes it possible to clearly and visually suggest a period to be noted in the analysis.

Note that, for example, the server 300 may automatically identify the corresponding period and provide the mark 633 or the user may manually provide the mark 633. To provide the mark 633 by the user, a method such as drag and drop can be adopted.

Furthermore, as illustrated in FIG. 11, a seek bar 634 arranged in parallel to the section images 631 and 632 may be provided in the progress status display area 620. By moving a slider 635 of the seek bar 634 along the time axis, the user may be able to control the reproduction position on the time axis of the surgical field video image reproduced in the in-OR video display area 650, the reproduction position on the time axis of the resource map reproduced in the resource map display area 660, and the display position on the time axis of the resource status displayed in the resource status display area 640.

As a result, it is possible to execute more detailed analysis only for a period desired to be focused on. Thus, the analysis work can be executed efficiently and in detail. For example, in a case where the surgery of gallbladder duct is performed in the surgical field video image in the case data, although it is the timing of cholecystectomy in the reference data, it is possible to easily recognize that the progress of surgery is relatively delayed.

2.6.4 Specific Example of Resource Status Display Area

Returning to FIG. 9 for the description, in the resource status display area 640, as described above, the status of the resources such as the surgeon, the staff, or the equipment in the work section selected is displayed in the progress status display area 620.

Specifically, for example, the utterance content ("sound (utterance)"), "work type", "in-room information", "movement information", "operating state", and the like are displayed as necessary for each resource such as "surgeon", "scopist", "scrub nurse", "circulating nurse", or "surgical instrument 1" to "surgical instrument 3".

By displaying the status of each resource, the user can confirm, for example, the possibility of discussion about the surgery policy from the sound waveform of the surgeon, the scopist, and the scrub nurse; the possibility of preparation for the next procedure from the work type information of the surgeon, the scopist, and the scrub nurse; the possibility of change of the nurse from the in-room information and the movement information of the scrub nurse and the circulating nurse; the possibility of waiting for replenishment of the instruments and the equipment of the circulating nurse from the in-room information and the movement information of the circulating nurse; and the possibility of occurrence of a trouble with the surgical instruments from the information on the circulating nurse and the surgical instruments according to visually obtained information.

Note that, when the user performing analysis selects a certain period in the mark 633 or the section image 631 in the work content display area 630 using a pointing device such as a mouse or a touch panel, a voice input system or a line-of-sight detection system (hereinafter referred to as an input device.), the status of the resources in the period corresponding to the mark 633 or the selected period may be displayed in the resource status display area 640. As a result, it is possible to easily identify the cause of the delay, and thus, the efficiency of the surgery-related service can be further easily improved.

In addition, the user can play back and reproduce the surgical field video image and the resource map considered to be highly relevant using the seek bar 634 and the slider 635 according to the hypothesis and the task set based on the resource status displayed in the resource status display area 640. Occurrence of the task can be easily confirmed from the surgical field video image played back and reproduced and the resource map.

2.6.5 Specific Example of in-OR Video Display Area

In the in-OR video display area 650, as described above, the surgical field video image acquired by the surgical field video image acquisition unit 203 of the data source 200 is reproduced as the time-varying data. Note that the surgical field video image reproduced in the in-OR video display area 650 may be, for example, the surgical field video image of the work section selected in the progress status display area 620. Furthermore, the position on the time axis of the surgical field video image being reproduced may be linked to the position of the slider 635 on the seek bar 634 in the work content display area 630. In other words, the movement of the slider 635 on the seek bar 634 over time may be synchronized with the reproduction of the surgical field video image in the in-OR video display area 650. The position on the time axis of the surgical field video image and the position of the slider 635 on the seek bar 634 may be associated with each other based on, for example, the tag information given to the section image 631. In other words, the tag information indicating a time-wise correlation may be added to the section image 631 and the surgical field video image. The tag information may be an index of the tag illustrated in FIG. 11 (also referred to as tag information).

Figure 12:
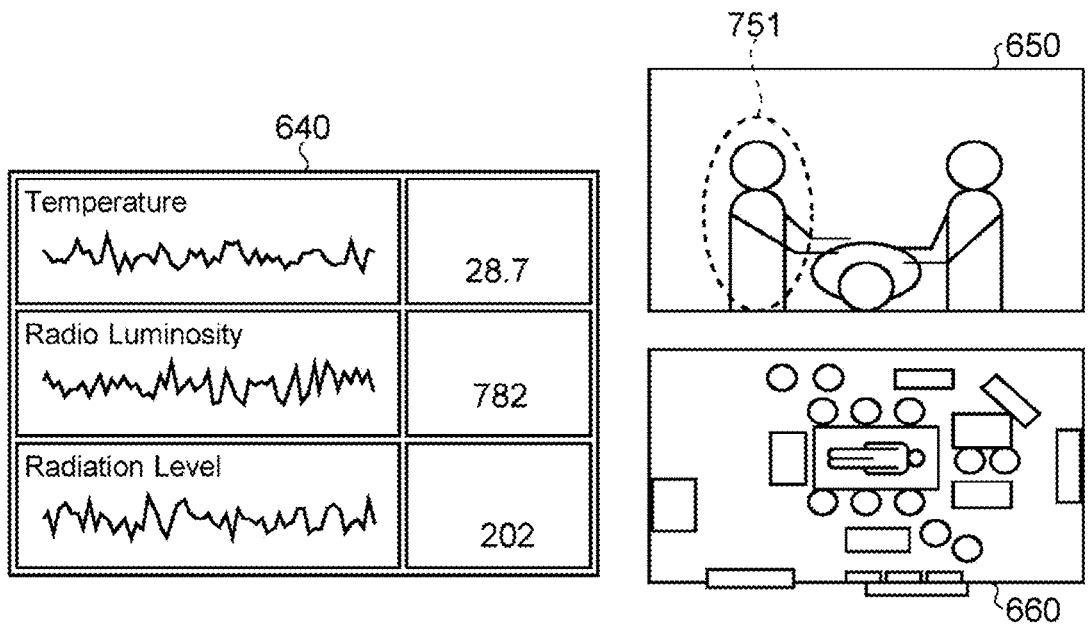
FIG. 12 is a diagram illustrating a specific example of an in-OR video display area and a resource status display area according to the embodiment of the present disclosure.

Furthermore, for example, the resources such as the surgeon, the staff, and the equipment included in the surgical field video image reproduced in the in-OR video display area 650 may function as icons 751 selectable by the user as illustrated in FIG. 12. An area in which the resource is projected in the visual field video may be determined, for example, by the surgery progress simulator 302 in the server 300.

When the user, using the input device, selects the icon 751 in the area in which a certain resource reproduced in the in-OR video display area 650 is displayed, the selected resource may be highlighted in the resource map display area 660 and the resource status display area 640.

Furthermore, when the icon 751 of a person such as the surgeon or the staff is selected, a flow line indicating a movement route of the selected person may be superimposed and displayed on the resource map display area 660.

Further, the resource status related to the selected resource and the status of the resource located around the selected resource may be displayed in the resource status display area 640 as time series data. As a result, the user can easily and visually grasp the status of individual resource and resources related to the individual resource, in addition to grasping the overall situation at a certain time point.

Note that the icon 751 superimposed on the visual-field video may be selectable according to the type of resource. For example, when a person category is selected as the target resource, an icon of the surgeon, the staff, or the like may be superimposed on the visual-field video. When an object category is selected, an icon of the equipment or the like may be superimposed on the visual-field video. As a result, even in a case where a person is in a blind spot of an object or vice versa, it is possible to select a resource that the user desires to select.

2.6.6 Specific Example of Resource Map Display Area

In the resource map display area 660, as described above, for example, the positions of resources such as the surgeon, the staff, and the equipment are reproduced on a two-dimensional map representing the operating room or the surgery-related facility including the operating room.

Figure 13:
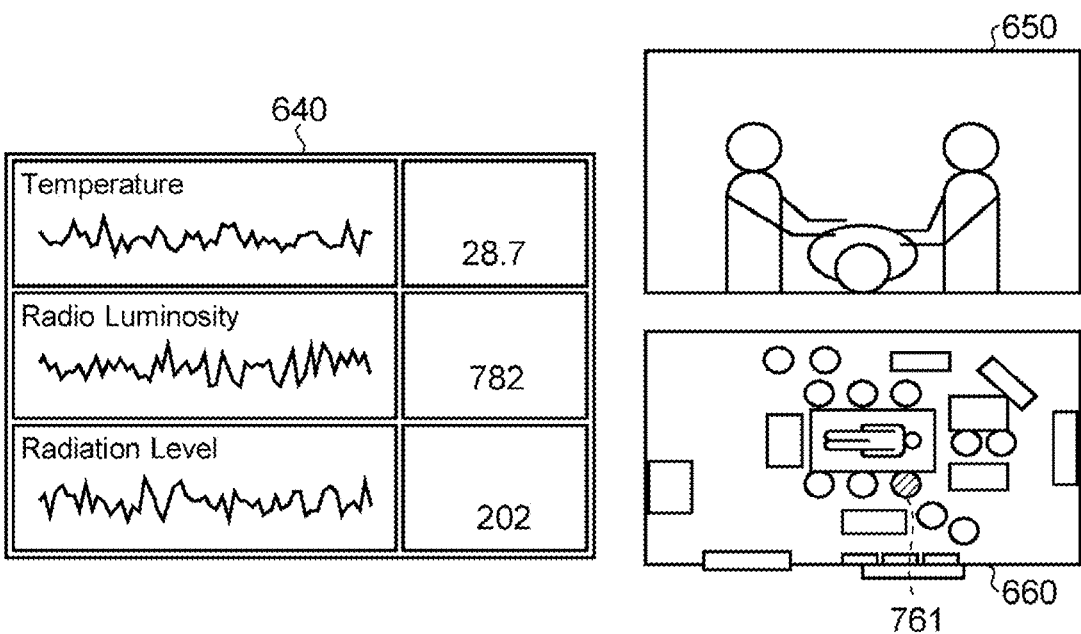
FIG. 13 is a diagram illustrating a specific example of a resource map display area and a resource status display area according to the embodiment of the present disclosure.

An item indicating the resource displayed in the resource map display area 660 may function as an icon 761 selectable by the user, for example, as illustrated in FIG. 13.

When the user selects the icon 761 of the resource displayed in the resource map display area 660 using the input device, the display of the selected resource may be highlighted in the in-OR video display area 650, the resource status display area 640, or the like. In addition, the video reproduced in the in-OR video display area 650 may be switched to the video in which the selected resource is displayed.

Furthermore, when the icon 761 of a person such as the surgeon or the staff is selected, the flow line indicating the movement route of the selected person may be superimposed and displayed on the resource map display area 660.

Further, the resource status related to the selected resource and the status of the resource located around the selected resource may be displayed in the resource status display area 640 as time series data. As a result, the user can easily and visually grasp the status of individual resource and resources related to the individual resource, in addition to grasping the overall situation at a certain time point.

Note that the icon 761 arranged in the resource map display area 660 may be selectable according to the type of resource. For example, when the person category is selected as the target resource, an icon such as the surgeon or the staff may be arranged in the resource map display area 660, and when the object category is selected, an icon such as the equipment may be arranged in the resource map display area 660. As a result, even in a case where the person and the object are superimposed, it is possible for the user to select the resource that the user wants to select.

2.7 Usage Examples of Surgery-Related Information Presentation Screen

2.7.1 Usage Example 1

Figure 14:
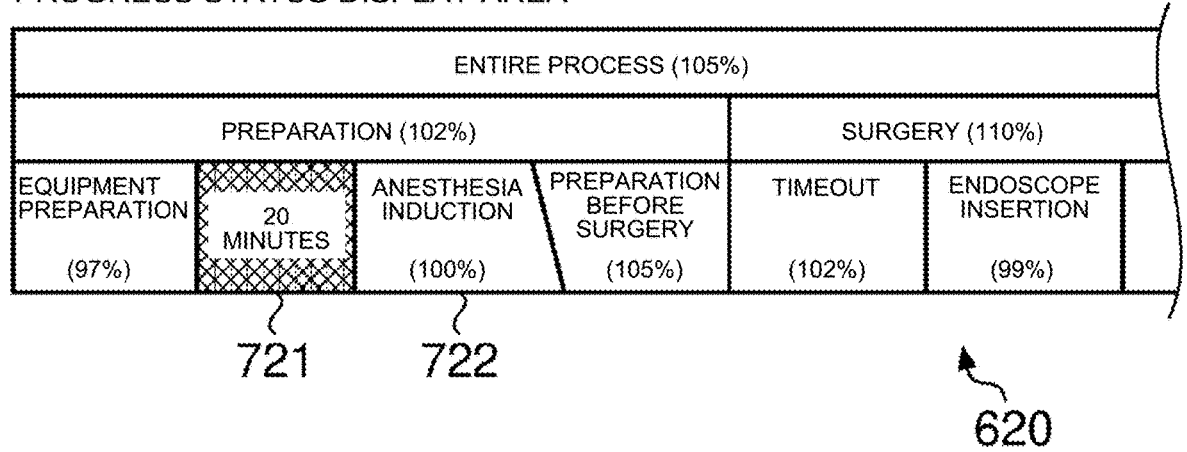
FIG. 14 is a diagram for explaining Usage Example 1 according to the embodiment of the present disclosure (part 1).

Note that, as illustrated in FIG. 14, when the case data is generated using the time-varying data obtained in the actual surgery, a blank section 721 in which nothing is performed may be displayed in the entire scene displayed in the progress status display area 620. In this case, when this blank section 721 is selected by the user, the resource status display area 640 may display a resource preparation status necessary for the start of a section next to the blank section 721, as illustrated in FIG. 15. For example, when the next section is for anesthesia induction 722, the resource statuses such as the "information transfer status" related to the "patient", the "in-room status" of the "anesthesiologist", and the "operating state" of the "anesthesia apparatus" may be displayed.

2.7.2 Usage Example 2

Figure 16:
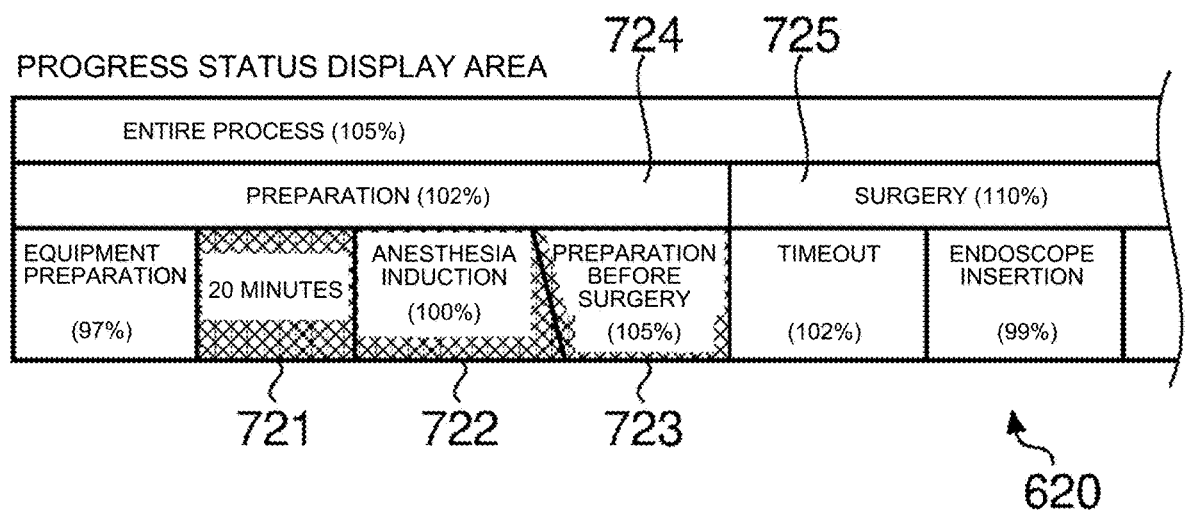
FIG. 16 is a diagram for explaining Usage Example 2 according to the embodiment of the present disclosure (part 1).

Furthermore, the occurrence of the blank section 721 may be caused not only by the next section (for example, anesthesia induction 722) but also by a section several steps ahead. Therefore, as illustrated in FIG. 16, a plurality of sections 721 to 723 including the blank section 721 may be selectable in the progress status display area 620.

When the plurality of sections 721 to 723 are selected in the progress status display area 620, as illustrated in FIG. 17, the resource status display area 640 may display the resource preparation status necessary for the start of each of the selected sections 722 and 723 other than the blank section 721 and a section next to the selected section. When the next section of the selected section is a different step, the resource preparation status necessary for starting the next step may be displayed. For example, when the last section 723 of the selected sections is the last section of a preparation step 724, the preparation status of resources required for the start of a surgical step 725, which is the next step to the preparation step 724, may be displayed.

By widening the selectable range in this way, it is possible to perform verification in a wide range so as to further accurately identify a delay factor. Note that the resource preparation status displayed in the resource status display area 640 may be configured to be settable by the user.

2.7.3 Usage Example 3

Figure 18:
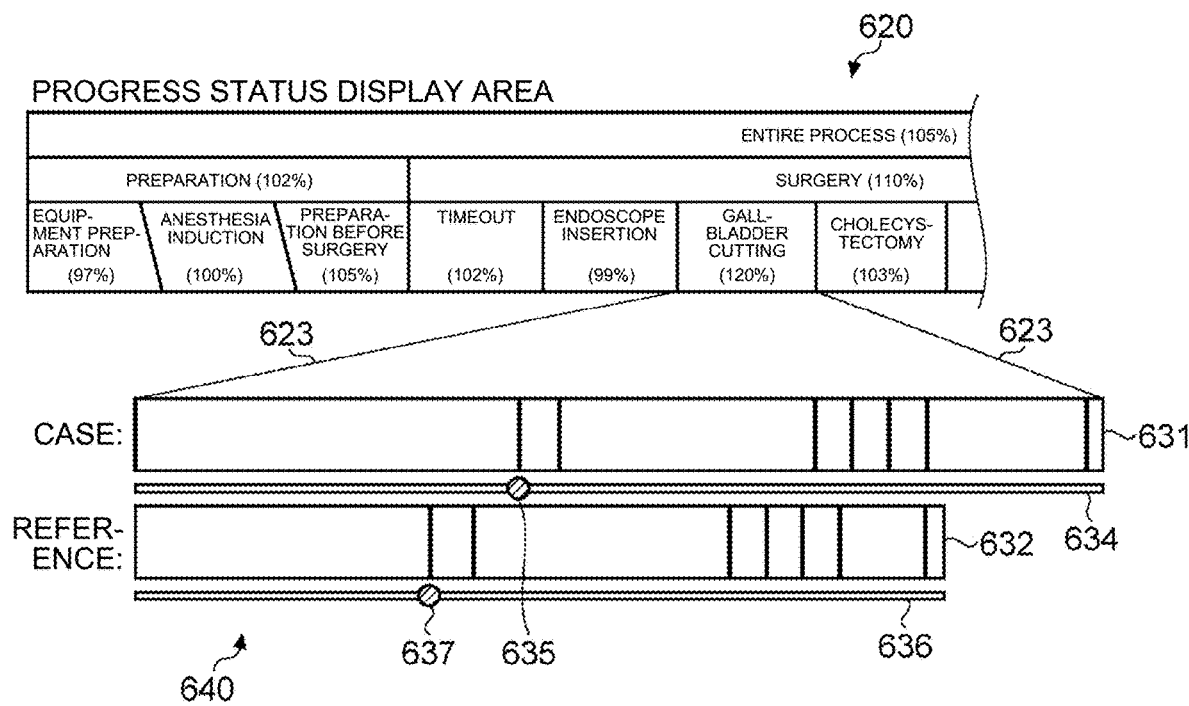
FIG. 18 is a diagram illustrating an example of the progress display area and the work content display area in Usage Example 3 according to the embodiment of the present disclosure.

FIG. 18 is a diagram illustrating an example of the progress status display area and the work content display area according to Usage Example 3 of the present embodiment. As illustrated in FIG. 18, in Usage Example 3, a seek bar 636 and a slider 637 are provided not only for the section image 631 of the case data but also for the section image 632 of the reference data. The position of the slider 637 on the seek bar 636 may be linked to the position of the slider 635 on the seek bar 634. In this case, the time axis of the seek bar 634 and the time axis of the seek bar 636 may be converted so that the slider 635 and the slider 637 will point corresponding works in the case data and the reference data. Linking between the position of the slider 637 on the seek bar 636 and the position of the slider 635 on the seek bar 634 may be performed based on the tag information added to each of the section images 631 and 632.

2.7.4 Usage Example 4

Figure 19:
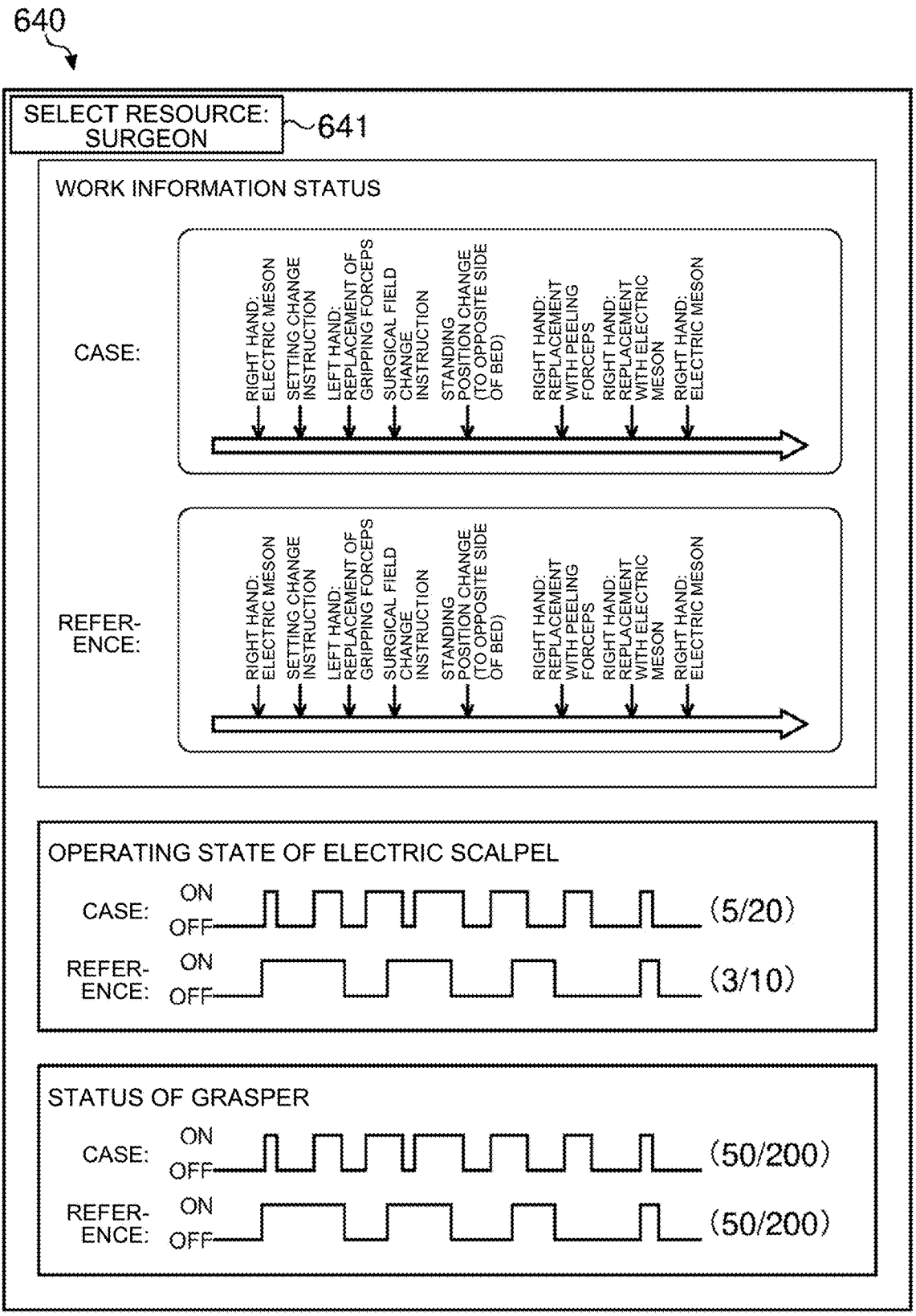
FIG. 19 is a diagram illustrating an example of the resource status display area in Usage Example 4 according to the embodiment of the present disclosure.

FIG. 19 is a diagram illustrating an example of the resource status display area according to Usage Example 4 of the present embodiment. As illustrated in FIG. 19, in Usage Example 4, a resource selection area 641 for the user to set resources to be displayed is provided in the resource status display area 640. As a method of selecting a resource to be displayed by the user, for example, various methods may be adopted, including a method in which selectable resources are listed by a pull-down menu and the user selects a resource from the list, and a method in which the user sets a resource by inputting a name of the resource desired to be displayed.

In this way, when the user can select the resource to be displayed, more detailed information of the selected resource may be displayed in the resource status display area 640. For example, when the selected resource is a person such as the surgeon or the staff, details of work content in the case data and the reference data may be displayed in parallel.

In addition, when the user can select the resource to be displayed, the status of a resource related to the selected resource may be displayed in the resource status display area 640. For example, when the selected resource is the surgeon, the operating state of the equipment to be used by the surgeon may be displayed.

2.7.5 Usage Example 5

Figure 20:
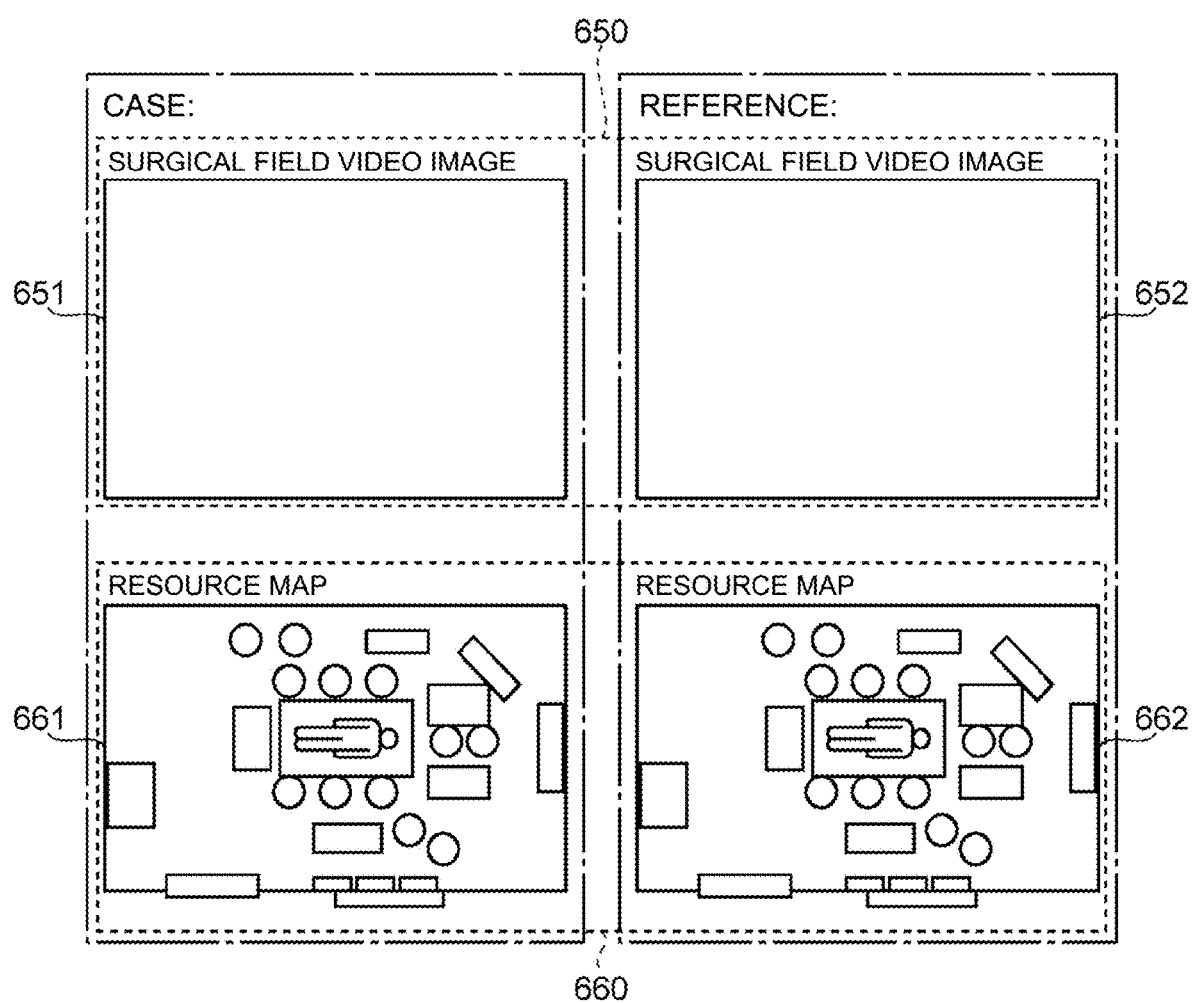
FIG. 20 is a diagram illustrating the example of the resource status display area in Usage Example 5 according to the embodiment of the present disclosure.

FIG. 20 is a diagram illustrating an example of the resource status display area according to Usage Example 5 of the present embodiment. As illustrated in FIG. 20, in Usage Example 5, surgical field video images 651 and 652 of the case data and the reference data are reproduced in the in-OR video display area 650. Reproduction time points of the surgical field video images 651 and 652 of the case data and the reference data may be synchronized, for example, based on the tag information attached to each of the section images 631 and 632.

In addition, as illustrated in FIG. 20, in Usage Example 5, a resource maps 661 and 662 of the case data and the reference data are reproduced in the resource map display area 660. Reproduction time points of the respective resource maps 661 and 662 of the case data and the reference data may be synchronized, for example, based on the tag information attached to the respective section images 631 and 632.

2.7.6 Usage Example 6

Figure 21:
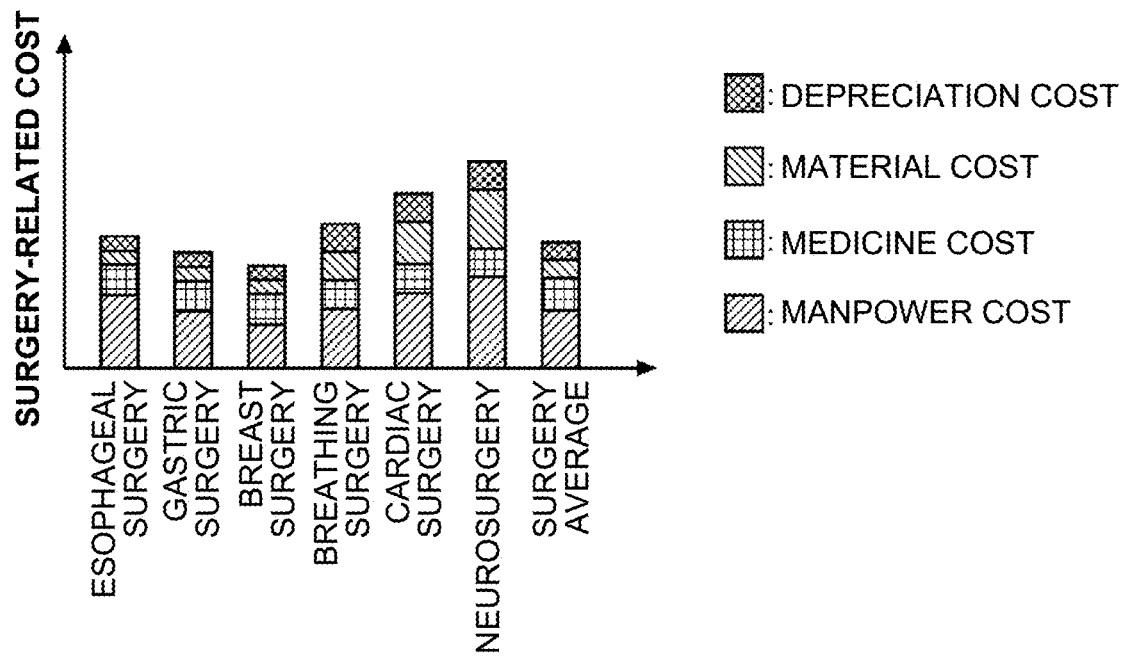
FIG. 21 is a diagram illustrating Usage Example 6 according to the embodiment of the present disclosure (part 1).
Figure 22:
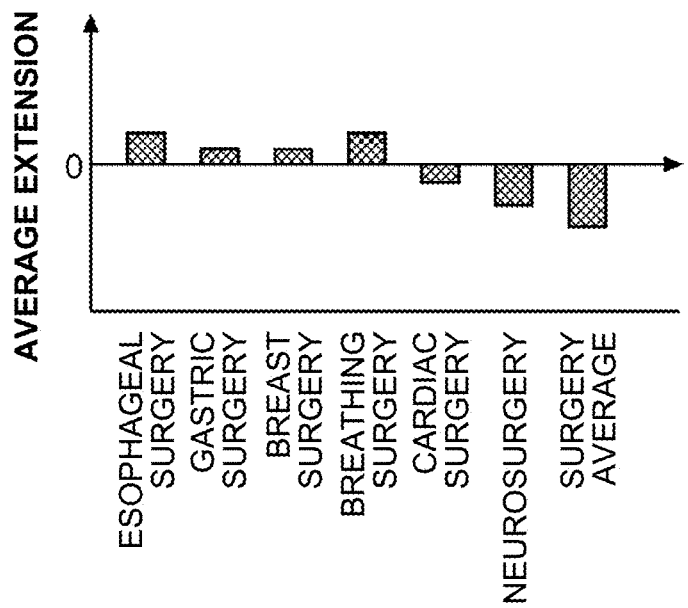
FIG. 22 is a diagram illustrating Usage Example 6 according to the embodiment of the present disclosure (part 2).

In addition, for example, when the user selects the case data or the reference data, a graph of the statistical information in the hospital created according to the non-time-varying data, as illustrated in FIG. 21 and FIG. 22, may be popped up. Note that FIG. 21 is an example of a statistical graph illustrating the surgery-related cost for each medical department, and FIG. 22 is an example of a statistical graph illustrating average delay time for each medical department.

By displaying the statistical information as described above at the time of selecting data, it is possible to set a target medical department that requires more efficiency. Thus, it is possible to provide more appropriate support for improving the efficiency.

Furthermore, when the user selects the case data or reference data, a surgery list as illustrated in FIG. 23 may be displayed. The surgery list may include not only the past surgeries but also currently ongoing surgery and surgeries scheduled in the future.

Furthermore, cases listed in the surgery list may be narrowed down to, for example, cases of the medical department selected by the user based on the graph illustrated in FIG. 21 or FIG. 22. In other words, the graph illustrated in FIG. 21 or FIG. 22 may also function as a user interface, and the user may be able to select a medical department with respect to applicable graph.

By displaying the surgery list, it is possible to reduce the time and effort required for the user to select a case. Furthermore, by including "surgery cost" and "surgery time" in items displayed in the list, it is also possible to allow the user to select optimal case data and reference data by verifying efficiency.

2.7.7 Usage Example 7

Furthermore, in the present embodiment, it is also possible to verify currently ongoing surgery in real time. FIG. 24 is a diagram illustrating an example of a part of the surgery-related information presentation screen according to the present embodiment when currently ongoing surgery is verified in real time. FIG. 24 illustrates an excerpt of the progress status display area 620, the work content display area 630, and the resource status display area 640.

As illustrated in FIG. 24, when the currently ongoing surgery is verified in real time, an indicator 623 such as an arrow indicating the progress up to the present may be displayed in the overall image 621 in the progress status display area 620.

In addition, for steps and sections that have not been started yet, an inconspicuous color may be used for display. For example, the color of a character string or a frame may be changed to gray, an outline character may be used, or a frame may be changed to a broken line.

Furthermore, for example, when the situation determination unit 402 determines that a delay has occurred in the progress of the surgery-related service, the information presentation processing unit 501 that has received the determination result from the situation determination unit 402 may notify a member outside the operating room, such as a chief nurse, of the delay. This notification may be made by, for example, sound, an image, or a character string, and a communication apparatus used in a hospital may be used as a terminal for receiving the notification. Note that a configuration for generating the notification may be, for example, the surgery progress simulator 302.

In the work content display area 630, a section image 631*a* including the tag of completed work in the currently ongoing surgery and a tagged section image 632 in the reference data may be displayed in parallel in the vertical direction. Furthermore, a time ratio with respect to work time in the reference data may be added to the tag attached to the section image 631*a* of the currently ongoing surgery. This makes it possible to more easily and visually recognize which work is currently delayed.

In the resource status display area 640, the resource status in the currently ongoing surgery may be displayed in real time. The user can determine, from the resource status displayed in real time, whether there is a high possibility of the presence of a staff who is waiting for the work or a staff who is not working. When there is a high possibility that these staffs are present, it is also possible to check the status of staffs concerned in real time, and notify the staffs to assist other staffs or start preparation for the next section ahead of the time.

As described above, by displaying the resource status in the currently ongoing surgery in real time, it is possible to identify, for example, the cause of delay in real time. For example, it is possible to identify from the resource status that there is a high possibility of forgetting to bringing in the equipment. In this case, for example, a nurse in the operating room may be notified of the fact. In addition, with this configuration, it is also possible to identify uninstalled equipment, or a possibility that the nurse is not efficiently performing the work from a long elapse of time from completion of the immediately preceding device installation or the work type and movement information of the nurse.

Note that, although not illustrated in FIG. 24, the surgical field video image and the resource map of the currently ongoing surgery may also be displayed in real time in the in-OR video display area 650 and the resource map display area 660.

2.8 Specific Example of Information Presentation Processing Unit

Figure 25:
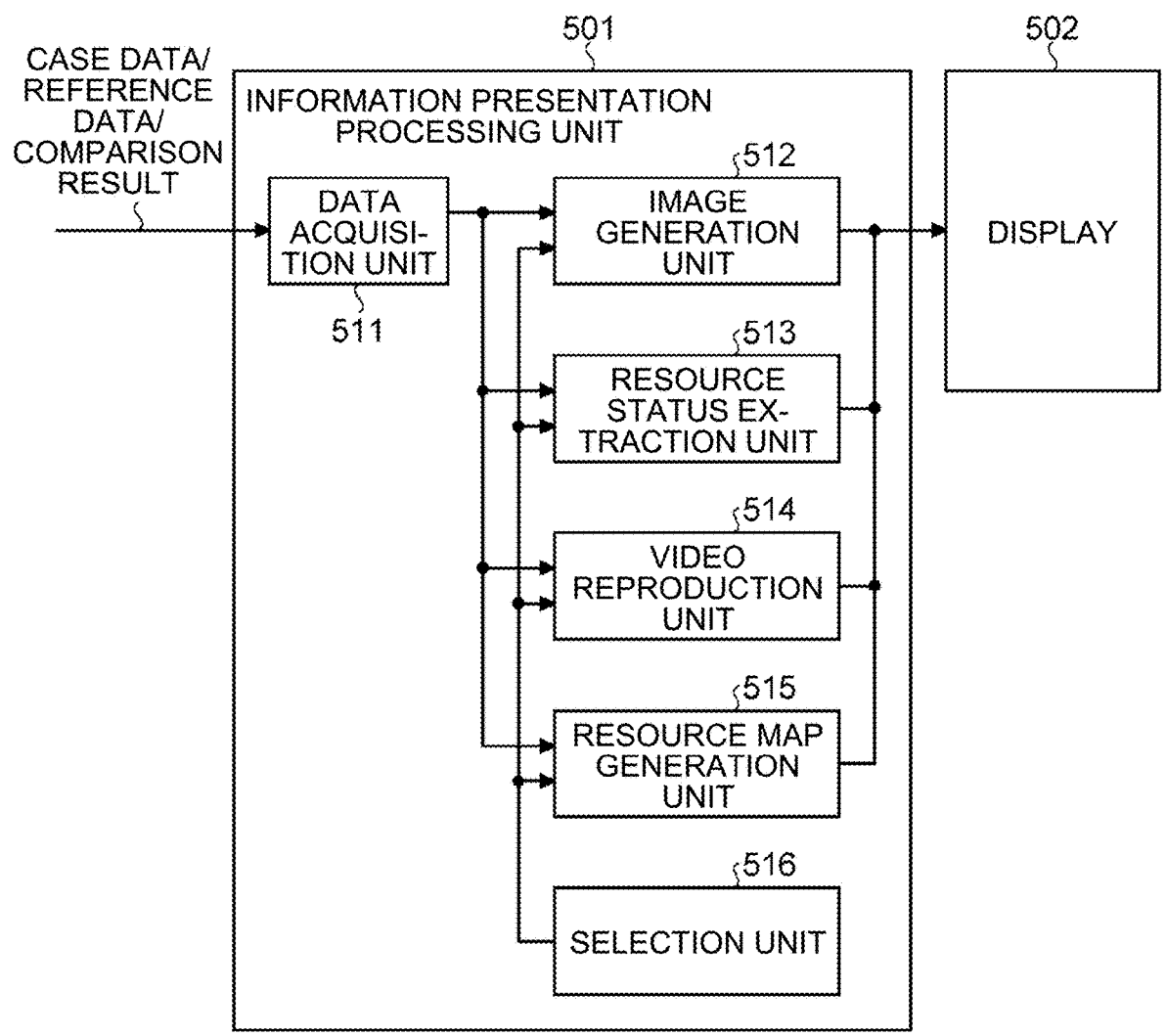
FIG. 25 is a block diagram illustrating a specific example of an information presentation processing unit according to the embodiment of the present disclosure.

Next, a specific example of the information presentation processing unit according to the present embodiment will be described in detail with reference to the drawings. FIG. 25 is a block diagram illustrating a configuration example of the information presentation processing unit according to the present embodiment. As illustrated in FIG. 25, the information presentation processing unit 501 includes a data acquisition unit 511 (surgery information acquisition unit), an image generation unit 512 (display control unit), a resource status extraction unit 513 (part of display control unit), a video reproduction unit 514 (part of display control unit), a resource map generation unit 515, and a selection unit 516.

The data acquisition unit 511 acquires, for example, the case data regarding surgery to be analyzed and the reference data regarding surgery to be compared. Specifically, the data acquisition unit 511 acquires the case data and the reference data accumulated in the database 301 as necessary. In addition, in real-time analysis of the currently ongoing surgery, the time-varying data acquired by the data source 200 is input to the data acquisition unit 511 via the data processing unit 401 and the situation determination unit 402.

Based on the case data acquired by the data acquisition unit 511, the image generation unit 512 generates a section image (for example, section image 631 illustrated in FIG. 18) representing each section for each work content in the series of steps of the surgery to be analyzed. Based on the reference data acquired by the data acquisition unit 511, the image generation unit 512 generates a section image (for example, section image 632 illustrated in FIG. 18) representing each section for each work content in the series of steps of the surgery to be compared. As described above, the section images generated by the image generation unit 512 are arranged in the vertical direction and displayed in parallel in the work content display area 630 of the surgery-related information presentation screen displayed on the display 502 as the display unit.

Here, the image generation unit 512 adjusts lengths in the time axis direction (horizontal direction in the drawings) of the section image generated from the case data and the section image generated from the reference data to lengths depending on the time required to complete the corresponding section. In addition, the image generation unit 512 matches the length per unit time between the section image generated from the case data and the section image generated from the reference data. This makes it possible to visually recognize how much each section in the analyzed surgery is shortened or delayed with respect to each section in the compared surgery.

The image generation unit 512 also generates the overall image 621 (for example, FIG. 10.) displaying sections of a series of surgical steps in the analyzed surgery based on the case data acquired by the data acquisition unit 511. As described above, the generated overall image 621 is displayed in the progress status display area 620 of the surgery-related information presentation screen displayed on display 502.

Furthermore, as described above, based on the resource status included in the case data, the image generation unit 512 may generate a section image of the analyzed surgery including the mark 633 (see FIG. 11) displaying a period in which the movement of the resource is not confirmed.

The image generation unit 512 may generate the overall image 621 so that each section in the overall image 621 functions as an icon selectable by the user. Selection of each section by the user may be input via the selection unit 516 that functions as the user interface and receives a section in the overall image 621 selected by the user. In addition, the section image displayed in the work content display area 630 may be a section image of the section selected by the user via the selection unit 516, or may be a section being executed in the currently ongoing surgery.

The time ratio of each section in the analyzed surgery with respect to each section in the compared surgery may be, for example, calculated by the situation determination unit 402. Then, based on a comparison result input from the situation determination unit 402, the image generation unit 512 may clearly indicate the time ratio of each section in the analyzed surgery with respect to each section in the compared surgery in the overall image 621. In addition, based on the comparison result input, the image generation unit 512 may generate the overall image 621 such that a section spending a longer time than the corresponding section in the compared surgery is highlighted.

The resource status extraction unit 513 extracts information regarding the status and position of the resource from the case data acquired by the data acquisition unit 511. Then, the resource status extraction unit 513 generates information displayed in the resource status display area 640 of the surgery-related information presentation screen displayed on the display 502 based on the extracted information.

The video reproduction unit 514 reproduces the surgical field video image of the case data acquired by the data acquisition unit 511 in the in-OR video display area 650 in the surgery-related information presentation screen displayed on the display 502.

The resource map generation unit 515 generates a resource map indicating the position of each resource in the currently selected section based on the information regarding the position of each resource in the case data acquired by the data acquisition unit 511, and displays the generated resource map in the resource map display area 660 of the surgery-related information presentation screen displayed on the display 502.

Note that, as described above, the resource status extraction unit 513 may generate information to be displayed in the resource status display area 640 such that the resource changes over time in accordance with the surgical field video image reproduced in the in-OR video display area 650. Similarly, the resource map generation unit 515 may generate the resource map such that the resource position changes over time in accordance with the surgical field video image reproduced in the in-OR video display area 650.

2.9 Effects

As described above, the information processing system according to the present embodiment is an information processing system capable of visualizing the management status in the OR, and can display the in-OR camera video, the in-hospital system information, the sensor information indicating equipment, positions and movements of person and equipment in the OR in real time or in an integrated manner with the past record information (statistical data).

In addition, the information processing system according to the present embodiment can simultaneously display one or more pieces of quantified information of the above-described information using characters and graphs together with the above-described camera image.

Furthermore, the information processing system according to the present embodiment can also analyze and compare each piece of equipment in the OR, movement or action history of the person in the real-time state and the record.

Furthermore, the information processing system according to the present embodiment can present information in different combinations such as by resource by time, and by case, in addition to the presentation of the current progress as a whole, and can present a time difference from the scheduled progress (past statistical data) for each resource to support management of the management progress.

Furthermore, the information processing system according to the present embodiment can easily present comparison with the recorded information (past statistical data) and support extraction of a cause and a task related to a time delay.

According to the information processing system, it is possible to determine a section that hinders the management numerically by quantifying various data groups in the OR. In addition, since they are linked to each resource in the video (multi-view or full-view video), it is possible to easily determine the actual work content by visual observation, image analysis, or the like. Accordingly, it is possible to identify, compare, and examine a detailed management status.

In addition, even in a case where it is difficult to perform uniform management (using manuals) because a plurality of staffs simultaneously performs different works and identification of each progress and team-work depends on individual skills or surrounding situations (patient background, surgery method, etc.), it is possible to view the progress status of all staffs in the OR in real time. In addition, it is possible to quantitatively identify the progress of each staff and all staffs by comparing with the past data (statistical information, simulation results, or the like). This allows other staffs inside and outside the OR to be involved, such as by an alert to delay. As a result, efficient management can be supported.

The technical scope of the present disclosure is not limited to the above-described embodiments, and various modifications can be made without departing from the gist of the present disclosure. In addition, components of different embodiments and modifications may be appropriately combined.

Note that the effects described in the present specification are merely examples and not limited thereto, and other effects may be provided.

The present technology can also have the following configurations.

(1)

An information processing system comprising:
a surgery information acquisition unit that acquires information regarding a surgery; and
a display control unit that executes control for displaying a surgery process area that indicates an entire process of the surgery and a degree of progress of the entire process, and a work process area that indicates a work content of a part of the entire process and a degree of progress of the work content, wherein
the display control unit calculates at least one of the degree of progress of the entire process and the degree of progress of the work content based on information regarding a surgery different from the surgery.

(2)

The information processing system according to (1), wherein the display control unit executes control for displaying in the surgery process area at least one first section obtained by dividing the entire process into processes according to the work content, and displaying in the work process area a second section obtained by dividing the first section into the work contents, the second section corresponding to one of the at least one first section in the work process area.

(3)

The information processing system according to (2), wherein the display control unit executes control for displaying the surgery process area and the work process area in an arrangement in parallel.

(4)

The information processing system according to (3), wherein the display control unit performs control to make a length in a vertical direction dependent on time with respect to the arrangement of the first section and the second section.

(5)

The information processing system according to any one of (2) to (4), further comprising:
- a first selection unit that receives selection by a user of the first section displayed in the surgery process area, wherein
- the display control unit executes control for displaying the work process area corresponding to the first section when the first selection unit receives the selection of the first section by the user.

(6)

The information processing system according to (5), further comprising:
- a comparison unit that compares the second section in the surgery and a corresponding second section in a surgery different from the surgery, wherein
- the display control unit executes control for highlighting the second section in the surgery that has a longer time for completion than the corresponding second section in the surgery different from the surgery, the highlighting being performed according to a comparison result of the comparison unit.

(7)

The information processing system according to any one of (2) to (6), wherein
- the information regarding the surgery includes information regarding a status of a resource used in the surgery, and
- the display control unit executes control for further displaying a resource display area that displays the information regarding the status of the resource in the second section.

(8)

The information processing system according to (7), wherein the resource includes at least one of a surgeon, a scopist, an anesthesiologist, and a nurse engaged in the surgery, and a surgical instrument used in the surgery.

(9)

The information processing system according to any one of (2) to (8), wherein
- the information regarding the surgery further includes a surgical field video image captured in the surgery, and
- the display control unit executes control for further displaying a video area that reproduces the surgical field video image.

(10)

The information processing system according to any one of (2) to (9), further comprising:
- a resource map generation unit that generates a resource map indicating a position of a resource in the second section based on information regarding the position of the resource used in the surgery, the information being included in the information regarding the surgery, wherein
- the display control unit executes control for further displaying a resource map area that displays the resource map generated by the resource map generation unit.

(11)

The information processing system according to any one of (2) to (6), further comprising:
- a resource map generation unit that generates a resource map indicating a position of a resource in the second section based on information regarding the position of the resource used in the surgery, the information being included in the information regarding the surgery, wherein
- the information regarding the surgery further includes information regarding a status of the resource used in the surgery and a surgical field video image captured in the surgery,
- the display control unit executes control for further displaying a resource display area that displays the information regarding the status of the resource in the second section, a video area that reproduces the surgical field video image, and a resource map area that displays the resource map generated by the resource map generation unit, and
- at least one of the information regarding the status of the resource displayed in the resource display area and the resource map displayed in the resource map area changes over time in line with the surgical field video image reproduced in the video area.

(12)

The information processing system according to any one of (2) to (11), further comprising:
- a resource map generation unit that generates a resource map indicating a position of a resource in the second section based on information regarding the position of the resource used in the surgery, the information being included in the information regarding the surgery, wherein
- the information regarding the surgery further includes information regarding a status of the resource used in the surgery and a surgical field video image captured in the surgery,
- the display control unit executes control for further displaying a resource display area that displays the information regarding the status of the resource in the second section, a video area that reproduces the surgical field video image, and a resource map area that displays the resource map generated by the resource map generation unit,
- a second selection unit that receives selection by a user of at least one of the resource included in the surgical field video image reproduced in the video area and the resource arranged on the resource map is further included, and
- the display control unit highlights the resource selected by the user via the second selection unit in at least one of the resource display area, the video area, and the resource map area.

(13)

The information processing system according to any one of (2) to (12), wherein
- the display control unit executes control for further displaying a period in which no movement of a resource is confirmed based on a status of the resource used in the surgery, the status being included in the information regarding the surgery.

(14)

The information processing system according to (13), wherein
- the information regarding the surgery includes information regarding the status of the resource used in the surgery, the display control unit further includes a resource display area that displays the information regarding the status of the resource in the second section, and the display control unit executes control for displaying the resource display area arranged adjacent to an arrangement of the surgery process area and the work process area.

(15)

An information processing method comprising:

acquiring information regarding a surgery;

calculating at least one of a degree of progress of an entire process of the surgery and a degree of progress of a work content of a part of the entire process, the calculation being made based on information regarding a surgery different from the surgery; and executing control for displaying a surgery process area that indicates the entire process and the degree of progress of the entire process, and a work process area that indicates the work content of the part of the entire process and the degree of the progress of the work content.

(16)

An information processing system comprising:

an information processing apparatus including a surgery information acquisition unit that acquires information regarding a surgery; and a program causing the information processing apparatus to execute a control function that executes control for displaying a surgery process area that indicates an entire process of the surgery and a degree of progress of the entire process, and a work process area that indicates a work content of a part of the entire process and a degree of progress of the work content, wherein the program further causes the information processing apparatus to execute calculating at least one of the degree of the progress of the entire process and the degree of the progress of the work content based on information regarding a surgery different from the surgery.

REFERENCE SIGNS LIST

1 INFORMATION PROCESSING SYSTEM
100 IN-HOSPITAL SYSTEM
101 OR SYSTEM
200 DATA SOURCE
201 SENSOR
202 IN-OR DEVICE
203 SURGICAL FIELD VIDEO IMAGE ACQUISITION UNIT
300 SERVER
301 DATABASE
302 SURGERY PROGRESS SIMULATOR
311 OR MANAGEMENT RESOURCE INFORMATION
312 RESOURCE SPECIFIC INFORMATION
400 PROCESSING DEVICE
401 DATA PROCESSING UNIT
402 SITUATION DETERMINATION UNIT
500 INFORMATION PRESENTATION SYSTEM
501 INFORMATION PRESENTATION PROCESSING UNIT
502 DISPLAY
511 DATA ACQUISITION UNIT
512 IMAGE GENERATION UNIT
513 RESOURCE STATUS EXTRACTION UNIT
514 VIDEO REPRODUCTION UNIT
515 RESOURCE MAP GENERATION UNIT
516 SELECTION UNIT
600 SURGERY-RELATED INFORMATION PRESENTATION SCREEN
610 DATA SELECTION AREA
620 PROGRESS DISPLAY AREA
621 OVERALL IMAGE
622 DIVIDING LINE
630 WORK CONTENT DISPLAY AREA
631, 632 SECTION IMAGE
633 MARK
634, 636 SEEK BAR
635, 637 SLIDER
640 RESOURCE STATUS DISPLAY AREA
650 IN-OR VIDEO DISPLAY AREA
651, 652 SURGICAL FIELD VIDEO IMAGE
660 RESOURCE MAP DISPLAY AREA
661, 662 RESOURCE MAP
721 BLANK SECTION
722 SECTION (ANESTHESIA INDUCTION)
723 SECTION (PREPARATION BEFORE SURGERY)
724 STEP (PREPARATION)
725 STEP (SURGERY)
751, 761 ICON

The invention claimed is:

1. An information processing system comprising:
circuitry configured to
acquire information regarding a surgery; and
execute control for displaying a surgery process area that indicates an entire process of the surgery and a degree of progress of the entire process, and a work process area that indicates a work content of a part of the entire process and a degree of progress of the work content, wherein
the circuitry is further configured to calculate at least one of the degree of progress of the entire process and the degree of progress of the work content based on information regarding a surgery different from the surgery.

2. The information processing system according to claim 1, wherein
the circuitry is further configured to execute control for displaying in the surgery process area at least one first section obtained by dividing the entire process into processes according to the work content, and displaying in the work process area a second section obtained by dividing the first section into the work contents, the second section corresponding to one of the at least one first section in the work process area.

3. The information processing system according to claim 2, wherein
the circuitry is further configured to execute control for displaying the surgery process area and the work process area in an arrangement in parallel.

4. The information processing system according to claim 3, wherein
the circuitry is further configured to perform control to make a length in a vertical direction dependent on time with respect to the arrangement of the first section and the second section.

5. The information processing system according to claim 2, wherein
the circuitry is further configured to receive selection by a user of the first section displayed in the surgery process area, and to execute control for displaying the work process area corresponding to the first section when the circuitry receives the selection of the first section by the user.

6. The information processing system according to claim 5, wherein
the circuitry is further configured to compare the second section in the surgery and a corresponding second section in a surgery different from the surgery,
and to execute control for highlighting the second section in the surgery that has a longer time for completion than the corresponding second section in the surgery different from the surgery, the highlighting being performed according to a comparison result of the circuitry.

7. The information processing system according to claim 2, wherein
the information regarding the surgery includes information regarding a status of a resource used in the surgery, and
the circuitry is further configured to execute control for further displaying a resource display area that displays the information regarding the status of the resource in the second section.

8. The information processing system according to claim 7, wherein
the resource includes at least one of a surgeon, a scopist, an anesthesiologist, and a nurse engaged in the surgery, and a surgical instrument used in the surgery.

9. The information processing system according to claim 2, wherein
the information regarding the surgery further includes a surgical field video image captured in the surgery, and
the circuitry is further configured to execute control for further displaying a video area that reproduces the surgical field video image.

10. The information processing system according to claim 2, wherein
the circuitry is further configured to generate a resource map indicating a position of a resource in the second section based on information regarding the position of the resource used in the surgery, the information being included in the information regarding the surgery,
and to execute control for further displaying a resource map area that displays the resource map that is generatedt.

11. The information processing system according to claim 2, wherein
the circuitry is further configured to generate a resource map indicating a position of a resource in the second section based on information regarding the position of the resource used in the surgery, the information being included in the information regarding the surgery,
the information regarding the surgery further includes information regarding a status of the resource used in the surgery and a surgical field video image captured in the surgery,
the circuitry is further configured to execute control for further displaying a resource display area that displays the information regarding the status of the resource in the second section, a video area that reproduces the surgical field video image, and a resource map area that displays the resource map that is generated, and
at least one of the information regarding the status of the resource displayed in the resource display area and the resource map displayed in the resource map area changes over time in line with the surgical field video image reproduced in the video area.

12. The information processing system according to claim 2, wherein
the circuitry is further configured to
generate a resource map indicating a position of a resource in the second section based on information regarding the position of the resource used in the surgery, the information being included in the information regarding the surgery, the information regarding the surgery further including information regarding a status of the resource used in the surgery and a surgical field video image captured in the surgery,
execute control for further displaying a resource display area that displays the information regarding the status of the resource in the second section, a video area that reproduces the surgical field video image, and a resource map area that displays the resource map that is generated,
receive selection by a user of at least one of the resource included in the surgical field video image reproduced in the video area and the resource arranged on the resource map, and
highlight the resource selected by the user in at least one of the resource display area, the video area, and the resource map area.

13. The information processing system according to claim 2, wherein
the circuitry is further configured to execute control for further displaying a period in which no movement of a resource is confirmed based on a status of the resource used in the surgery, the status being included in the information regarding the surgery.

14. The information processing system according to claim 13, wherein
the information regarding the surgery includes information regarding the status of the resource used in the surgery, and
the circuitry is further configured to execute control for further displaying a resource display area that displays the information regarding the status of the resource in the second section,
the resource display area being arranged adjacent to an arrangement of the surgery process area and the work process area.

15. An information processing method, executed by circuitry of an information processing system, the information processing method comprising:
acquiring information regarding a surgery;
calculating at least one of a degree of progress of an entire process of the surgery and a degree of progress of a work content of a part of the entire process, the calculation being made based on information regarding a surgery different from the surgery; and
executing control for displaying on a display a surgery process area that indicates the entire process and the degree of progress of the entire process, and a work process area that indicates the work content of the part of the entire process and the degree of the progress of the work content.

16. An information processing system comprising:
an information processing apparatus including circuitry configured to acquire information regarding a surgery; and
a program causing the information processing apparatus to execute a control function that executes control for displaying a surgery process area that indicates an entire process of the surgery and a degree of progress of the entire process, and a work process area that indicates a work content of a part of the entire process and a degree of progress of the work content, wherein the program further causes the information processing apparatus to execute calculating at least one of the degree of the progress of the entire process and the degree of the progress of the work content based on information regarding a surgery different from the surgery.

* * * * *